(12) United States Patent
LaRose et al.

(10) Patent No.: US 9,339,598 B2
(45) Date of Patent: *May 17, 2016

(54) AXIAL FLOW PUMP WITH MULTI-GROOVED ROTOR

(71) Applicant: HeartWare, Inc., Miami Lakes, FL (US)

(72) Inventors: Jeffrey A. LaRose, Sunrise, FL (US); Charles R. Shambaugh, Jr., Coral Gables, FL (US); Kartikeyan Trichi, Miami Lakes, FL (US); Richard A. Marquis, Miami, FL (US); Daniel G. White, Folsom, CA (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,971

(22) Filed: Jul. 10, 2014

(65) Prior Publication Data

US 2015/0038769 A1 Feb. 5, 2015

Related U.S. Application Data

(63) Continuation of application No. 11/992,997, filed as application No. PCT/US2006/021544 on Jun. 2, 2006, now Pat. No. 8,790,236, which is a continuation of application No. 11/243,722, filed on Oct. 5, 2005, now Pat. No. 8,419,609.

(30) Foreign Application Priority Data

Oct. 6, 2005 (WO) .................. PCT/US2005/03596
Nov. 22, 2005 (WO) .................. PCT/US2005/04249

(51) Int. Cl.
*A61M 1/10* (2006.01)
*A61M 1/12* (2006.01)

(52) U.S. Cl.
CPC ............. *A61M 1/1029* (2014.02); *A61M 1/101* (2013.01); *A61M 1/1008* (2014.02); *A61M 1/1015* (2014.02); *A61M 1/1017* (2014.02); *A61M 1/1031* (2014.02); *A61M 1/1036* (2014.02); *A61M 1/122* (2014.02); *A61M 1/125* (2014.02)

(58) Field of Classification Search
CPC . A61M 1/101; A61M 1/1015; A61M 1/1029; A61M 1/1036; A61M 1/122; A61M 1/125
See application file for complete search history.

(56) References Cited

U.S. PATENT DOCUMENTS

| 50,714 A | 10/1865 | Fritz |
| 2,941,477 A | 6/1960 | Dalton |

(Continued)

FOREIGN PATENT DOCUMENTS

| CN | 1278188 A | 12/2000 |
| GB | 1067054 A | 4/1967 |

(Continued)

OTHER PUBLICATIONS

"MMPA Standard No. 0100-00; Standard Specifications for Permanent Magnet Materials," (1996) Magnet Material Producers Association, pp. 1-28.

(Continued)

*Primary Examiner* — Joseph Dietrich
(74) *Attorney, Agent, or Firm* — Lerner, David, Littenberg, Krumholz & Mentlik, LLP

(57) ABSTRACT

An axial-flow blood pump for pumping blood includes a substantially cylindrical outer enclosure. A tubular housing concentric with and located within the outer enclosure has at one end an inlet and at an opposite end an outlet. A motor stator is concentric with and located between the outer enclosure and the tubular housing. An impeller is concentric with and located within the tubular housing. The impeller is suspended in operation by a combination of passive magnetic forces between magnets within the impeller or magnetized regions of the impeller and the motor stator and hydrodynamic thrust forces generated as blood flows between the tubular housing and a plurality of hydrodynamic thrust bearing surfaces located on the impeller. A volute may be in fluid-tight connection with the outlet of the tubular housing for receiving blood in the axial direction and directing blood in a direction normal to the axial direction. The volute has a flow-improving member extending axially from the volute and into and coaxially with the tubular housing.

20 Claims, 29 Drawing Sheets

(56) References Cited

U.S. PATENT DOCUMENTS

| | | |
|---|---|---|
| 3,426,721 A | 2/1969 | Justinien |
| 3,608,088 A | 9/1971 | Dorman et al. |
| 3,685,059 A | 8/1972 | Bokros et al. |
| 4,437,815 A | 3/1984 | McMullen |
| 4,589,822 A | 5/1986 | Clausen et al. |
| 4,595,390 A | 6/1986 | Hakim et al. |
| 4,615,691 A | 10/1986 | Hakim et al. |
| 4,625,712 A | 12/1986 | Wampler |
| 4,642,036 A | 2/1987 | Young |
| 4,688,998 A | 8/1987 | Olsen et al. |
| 4,753,221 A | 6/1988 | Kensey et al. |
| 4,779,614 A | 10/1988 | Moise |
| 4,817,586 A | 4/1989 | Wampler |
| 4,846,152 A | 7/1989 | Wampler et al. |
| 4,863,461 A | 9/1989 | Jarvik |
| 4,906,229 A | 3/1990 | Wampler |
| 4,908,012 A | 3/1990 | Moise et al. |
| 4,919,647 A | 4/1990 | Nash |
| 4,927,407 A | 5/1990 | Dorman |
| 4,944,722 A | 7/1990 | Carriker et al. |
| 4,957,504 A | 9/1990 | Chardack |
| 4,994,078 A | 2/1991 | Jarvik |
| 4,995,857 A | 2/1991 | Arnold |
| 5,061,256 A | 10/1991 | Wampler |
| 5,092,879 A | 3/1992 | Jarvik |
| 5,112,200 A | 5/1992 | Isaacson et al. |
| 5,209,650 A | 5/1993 | Lemieux |
| 5,211,546 A | 5/1993 | Isaacson et al. |
| 5,290,227 A | 3/1994 | Pasque |
| 5,290,236 A | 3/1994 | Mathewson |
| 5,344,443 A | 9/1994 | Palma et al. |
| 5,376,114 A | 12/1994 | Jarvik |
| 5,385,581 A | 1/1995 | Bramm et al. |
| 5,501,574 A | 3/1996 | Raible |
| 5,527,159 A | 6/1996 | Bozeman, Jr. et al. |
| 5,588,812 A | 12/1996 | Taylor et al. |
| 5,613,935 A | 3/1997 | Jarvik |
| 5,678,306 A | 10/1997 | Bozeman, Jr. et al. |
| 5,692,882 A | 12/1997 | Bozeman, Jr. et al. |
| 5,707,218 A | 1/1998 | Maher et al. |
| 5,713,727 A | 2/1998 | Veronesi et al. |
| 5,746,709 A | 5/1998 | Rom et al. |
| 5,776,190 A | 7/1998 | Jarvik |
| 5,824,070 A | 10/1998 | Jarvik |
| 5,840,070 A | 11/1998 | Wampler |
| 5,851,174 A | 12/1998 | Jarvik et al. |
| 5,868,763 A | 2/1999 | Spence et al. |
| 5,888,241 A | 3/1999 | Jarvik |
| 5,911,685 A | 6/1999 | Siess et al. |
| 5,924,848 A | 7/1999 | Izraelev |
| 5,941,813 A | 8/1999 | Sievers et al. |
| 5,947,892 A | 9/1999 | Benkowski et al. |
| 5,965,089 A | 10/1999 | Jarvik et al. |
| 6,015,272 A | 1/2000 | Antaki et al. |
| 6,019,722 A | 2/2000 | Spence et al. |
| 6,053,705 A | 4/2000 | Schob et al. |
| 6,058,593 A | 5/2000 | Siess |
| 6,068,588 A | 5/2000 | Goldowsky |
| 6,100,618 A | 8/2000 | Schoeb et al. |
| 6,116,862 A | 9/2000 | Rau et al. |
| 6,120,537 A | 9/2000 | Wampler |
| 6,135,729 A | 10/2000 | Aber |
| 6,155,969 A | 12/2000 | Schima et al. |
| 6,162,233 A | 12/2000 | Williamson, IV et al. |
| 6,176,822 B1 | 1/2001 | Nix et al. |
| 6,190,397 B1 | 2/2001 | Spence et al. |
| 6,200,260 B1 | 3/2001 | Bolling |
| 6,227,797 B1 | 5/2001 | Watterson et al. |
| 6,227,820 B1 | 5/2001 | Jarvik |
| 6,234,635 B1 | 5/2001 | Seitzinger et al. |
| 6,234,772 B1 | 5/2001 | Wampler et al. |
| 6,234,998 B1 | 5/2001 | Wampler |
| 6,244,835 B1 | 6/2001 | Antaki et al. |
| 6,247,892 B1 | 6/2001 | Kazatchkov et al. |
| 6,250,880 B1 | 6/2001 | Woodard et al. |
| 6,254,359 B1 | 7/2001 | Aber |
| 6,254,617 B1 | 7/2001 | Spence et al. |
| 6,299,575 B1 | 10/2001 | Bolling |
| 6,306,116 B1 | 10/2001 | Hancock |
| 6,368,083 B1 | 4/2002 | Wampler |
| 6,387,037 B1 | 5/2002 | Bolling et al. |
| 6,390,969 B1 | 5/2002 | Bolling et al. |
| 6,419,696 B1 | 7/2002 | Ortiz et al. |
| 6,428,464 B1 | 8/2002 | Bolling |
| 6,439,845 B1 | 8/2002 | Veres |
| 6,447,265 B1 | 9/2002 | Antaki et al. |
| 6,447,266 B2 | 9/2002 | Antaki et al. |
| 6,488,692 B1 | 12/2002 | Spence et al. |
| 6,527,521 B2 | 3/2003 | Noda |
| 6,527,699 B1 | 3/2003 | Goldowsky |
| 6,530,876 B1 | 3/2003 | Spence |
| 6,581,476 B1 | 6/2003 | Fremerey |
| 6,595,743 B1 | 7/2003 | Kazatchkov et al. |
| 6,610,004 B2 | 8/2003 | Viole et al. |
| 6,610,008 B1 | 8/2003 | Spence et al. |
| 6,619,291 B2 | 9/2003 | Hlavka et al. |
| 6,641,378 B2 | 11/2003 | Davis et al. |
| 6,652,543 B2 | 11/2003 | Spence et al. |
| 6,659,270 B2 | 12/2003 | Williamson, IV et al. |
| 6,685,621 B2 | 2/2004 | Bolling et al. |
| 6,688,661 B2 | 2/2004 | Yamamoto |
| 6,688,861 B2 | 2/2004 | Wampler |
| 6,716,157 B2 | 4/2004 | Goldowsky |
| 6,716,189 B1 | 4/2004 | Jarvik et al. |
| 6,717,311 B2 | 4/2004 | Locke |
| 6,719,791 B1 | 4/2004 | Nusser et al. |
| 6,730,121 B2 | 5/2004 | Ortiz et al. |
| 6,742,999 B1 | 6/2004 | Nusser et al. |
| 6,752,602 B2 | 6/2004 | Schulte Eistrup et al. |
| 6,794,789 B2 | 9/2004 | Siess et al. |
| 6,869,567 B2 | 3/2005 | Kretchmer |
| 6,889,082 B2 | 5/2005 | Bolling et al. |
| 7,011,620 B1 | 3/2006 | Siess |
| 7,021,905 B2 | 4/2006 | Torrey et al. |
| 7,070,398 B2 | 7/2006 | Olsen et al. |
| 7,229,258 B2 | 6/2007 | Wood et al. |
| 7,699,586 B2 | 4/2010 | LaRose et al. |
| 7,972,122 B2 | 7/2011 | LaRose et al. |
| 8,007,254 B2 | 8/2011 | LaRose et al. |
| 8,419,609 B2 | 4/2013 | Shambaugh, Jr. et al. |
| 8,668,473 B2 | 3/2014 | LaRose et al. |
| 8,790,236 B2 | 7/2014 | LaRose et al. |
| 2001/0031210 A1 | 10/2001 | Antaki et al. |
| 2003/0091450 A1 | 5/2003 | Davis et al. |
| 2004/0241019 A1 | 12/2004 | Goldowsky |
| 2004/0265153 A1 | 12/2004 | Torrey et al. |
| 2005/0107657 A1 | 5/2005 | Carrier et al. |
| 2005/0135942 A1 | 6/2005 | Wood et al. |
| 2006/0036127 A1 | 2/2006 | Delgado |
| 2006/0245959 A1 | 11/2006 | LaRose et al. |
| 2007/0078293 A1 | 4/2007 | Shambaugh et al. |
| 2007/0100196 A1 | 5/2007 | LaRose et al. |
| 2010/0069847 A1 | 3/2010 | LaRose et al. |
| 2011/0301403 A1 | 12/2011 | LaRose et al. |
| 2015/0031936 A1 | 1/2015 | LaRose et al. |

FOREIGN PATENT DOCUMENTS

| | | |
|---|---|---|
| JP | 2004278375 A | 10/2004 |
| WO | 2005030296 A2 | 4/2005 |
| WO | 2005032620 A1 | 4/2005 |
| WO | 2006060260 A2 | 6/2006 |
| WO | 2006118600 A2 | 11/2006 |

OTHER PUBLICATIONS

Advisory Action issued Apr. 27, 2009 in connection with U.S. Appl. No. 11/003,810, filed Dec. 3, 2004.
Advisory Action issued Feb. 12, 2010 in connection with U.S. Appl. No. 11/118,551, filed Apr. 29, 2005.
Advisory Action issued Feb. 28, 2011 in connection with U.S. Appl. No. 11/243,722, filed Oct. 5, 2005.
Advisory Action issued Feb. 29, 2012 in connection with U.S. Appl. No. 11/243,722, filed Oct. 5, 2005.

(56) References Cited

OTHER PUBLICATIONS

Advisory Action issued Jan. 26, 2010 in connection with U.S. Appl. No. 11/243,722, filed Oct. 5, 2005, 3 pgs.
Advisory Action issued Oct. 14, 2008 in connection with U.S. Appl. No. 11/243,722, filed Oct. 5, 2005, 4 pgs.
Communication issued Nov. 7, 2013 by the European Patent Office in connection with European Patent Application No. 06772018.5.
Final Office Action issued Aug. 16, 2010 in connection with U.S. Appl. No. 11/445,963, filed Jun. 2, 2006, 13 pgs.
Final Office Action issued Dec. 10, 2008 in connection with U.S. Appl. No. 11/003,810, filed Dec. 3, 2004.
Final Office Action issued Jun. 20, 2008 in connection with U.S. Appl. No. 11/243,722, filed Oct. 5, 2005, 9 pgs.
Final Office Action issued Nov. 18, 2009 in connection with U.S. Appl. No. 11/118,551, filed Apr. 29, 2005.
Final Office Action issued Oct. 23, 2008 in connection with U.S. Appl. No. 11/118,551, filed Apr. 29, 2005, 15 pgs.
Final Office Action issued Sep. 28, 2011 in connection with U.S. Appl. No. 11/243,722, filed Oct. 5, 2005.
Final Office Action issued Sep. 13, 2010 in connection with U.S. Appl. No. 11/243,722, filed Oct. 5, 2005, 10 pgs.
Final Office Action issued Sep. 30, 2009 in connection with U.S. Appl. No. 11/243,722, filed Oct. 5, 2005, 10 pgs.
Humphrey, Bruce "Coatings—Using Parylene for Medical Substrate Coating", www.devicelink.com/ (Jan. 1996) 5 pages.
International Preliminary Report on Patentability for PCT/US05/42495, dated Apr. 17, 2008, 9 pgs.
International Preliminary Report on Patentability issued by the International Bureau of WIPO on Apr. 8, 2008 in connection with International Application No. PCT/US2006/21544, dated Dec. 16, 2006, 6 pgs.
International Search Report issued Apr. 17, 2008 by the International Searching Authority (ISA/US) in connection with International Application No. PCT/US2005/42495.
International Search Report issued Aug. 20, 2007 by the International Searching Authority (ISA/US) in connection with International Application No. PCT/US2005/35964.
International Search Report issued by the International Searching Authority (ISA/US) in connection with International Application No. PCT/US2006/21544, dated Dec. 13, 2006, 2 pgs.
Notice of Allowance issued Aug. 28, 2009 in connection with U.S. Appl. No. 11/003,810, filed Dec. 3, 2004.
Notice of Allowance issued Dec. 9, 2010 in connection with U.S. Appl. No. 11/118,551, filed Apr. 29, 2005.
Notice of Allowance issued Feb. 17, 2011 in connection with U.S. Appl. No. 11/445,963, filed Jun. 2, 2006, 9 pgs.
Notice of Allowance issued Jan. 31, 2013 in connection with U.S. Appl. No. 11/243,772, filed Oct. 5, 2005.
Notice of Allowance issued Jan. 12, 2010 in connection with U.S. Appl. No. 11/003,810, filed Dec. 3, 2004.
Office Action issued Apr. 17, 2009 in connection with U.S. Appl. No. 11/118,551, filed Apr. 29, 2005, 17 pgs.
Office Action issued Dec. 19, 2008 in connection with U.S. Appl. No. 11/243,722, filed Oct. 5, 2005, 9 pgs.
Office Action issued Jan. 19, 2010 in connection with U.S. Appl. No. 11/445,963, filed Jun. 2, 2006, 10 pgs.
Office Action issued Jul. 12, 2010 in connection with U.S. Appl. No. 11/118,551, filed Apr. 29, 2005.
Office Action issued Mar. 29, 2011 in connection with U.S. Appl. No. 11/243,722, filed Oct. 5, 2005.
Office Action issued Mar. 11, 2013 in connection with U.S. Appl. No. 13/212,014, filed Aug. 17, 2011.
Office Action issued Mar. 17, 2008 in connection with U.S. Appl. No. 11/003,810, filed Dec. 3, 2004.
Office Action issued Mar. 20, 2008 in connection with U.S. Appl. No. 11/118,551, filed Apr. 29, 2005, 11 pgs.
Office Action issued Mar. 24, 2010 in connection with U.S. Appl. No. 11/243,722, filed Oct. 5, 2005, 10 pgs.
Office Action issued Oct. 3, 2012 in connection with U.S. Appl. No. 11/243,722, filed Oct. 5, 2005.
Office Action issued Sep. 10, 2007 in connection with U.S. Appl. No. 11/243,722, filed Oct. 5, 2005, 13 pgs.
Office Action issued Sep. 22, 2009 in connection with U.S. Appl. No. 11/445,963, filed Jun. 2, 2006, 8 pgs.
Office Action issued Sep. 28, 2012 in connection with U.S. Appl. No. 13/212,014, filed Aug. 17, 2011.
Olsen, Don B., Presidential Address—The History of Continuous-Flow Blood Pumps. Artificial Organs 24(6), 401-404, Mar. 2000.
Siegenthaler et al. "Mechanical Circulatory Assistance for Acute and Chronic Heart Failure: a Review of Current Technology & Clinical Practice", Journal of Interventional Cardiology, vol. 16/No. 6 (2003) pp. 563-572.
Song et al., (2003) Axial Flow Blood Pumps. ASAIO Journal 2003, 355-364.
Written Opinion of the International Searching Authority issued by the International Searching Authority (ISA/US) in connection with International Application No. PCT/US2005/35964, dated Aug. 20, 2007, 3 pgs.
Written Opinion of the International Searching Authority issued Dec. 13, 2006 by the International Searching Authority (ISA/US) in connection with International Application No. PCT/US2006/21544.
Chinese Office Action for Application No. 201210244769.9 dated Jul. 28, 2014.
Chinese Office Action for Application No. 201210073420.3 dated Jun. 5, 2014.
International Search Report issued by the International Searching Authority (ISA/US) in connection with International Application No. PCT/US2005/35964, dated Aug. 20, 2007, 2 pgs.
MMPA Standard No. 0100-00; Standard Specifications for Permanent Magnet Materials; (Magnetic Material Producers Association; (28 pgs), Jun. 6, 2006.
Notice of Allowability issued Oct. 21, 2013 in connection with U.S. Appl. No. 13/212,014, filed Aug. 17, 2011.
Notice of Allowance issued Jan. 24, 2013 in connection with U.S. Appl. No. 11/992,997, filed Apr. 1, 2008.
Office Action issued Dec. 27, 2011 in connection with U.S. Appl. No. 11/992,997, filed Apr. 1, 2008.
Response to Office Action issued Mar. 11, 2013, filed Jun. 7, 2013, in connection with U.S. Appl. No. 13/212,014, filed Aug. 17, 2011.
Response to Office Action issued Sep. 28, 2012, filed Nov. 26, 2012, in connection with U.S. Appl. No. 13/212,014, filed Aug. 17, 2011.
Written Opinion for International Application No. PCT/US05/42495, dated Apr. 17, 2008, 7 pgs.
Written Opinion of the International Searching Authority issued by the International Searching Authority (ISA/US) in connection with International Application No. PCT/US2005/42495, Apr. 17, 2008.
Australian Examination Report for Application No. 2013257469 dated May 21, 2015.
European Examination Report for Application No. 06772018.5 dated Oct. 15, 2015.

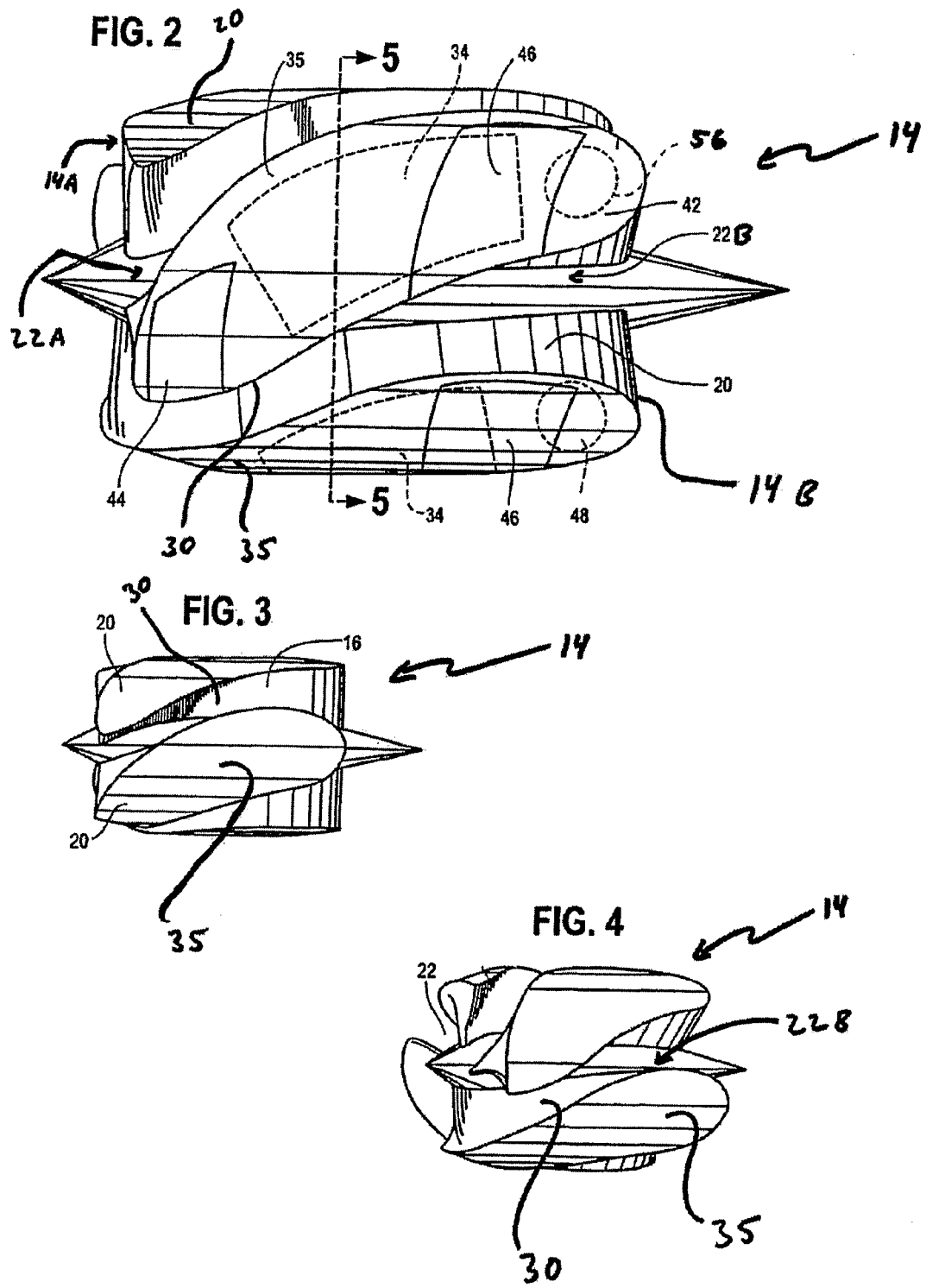

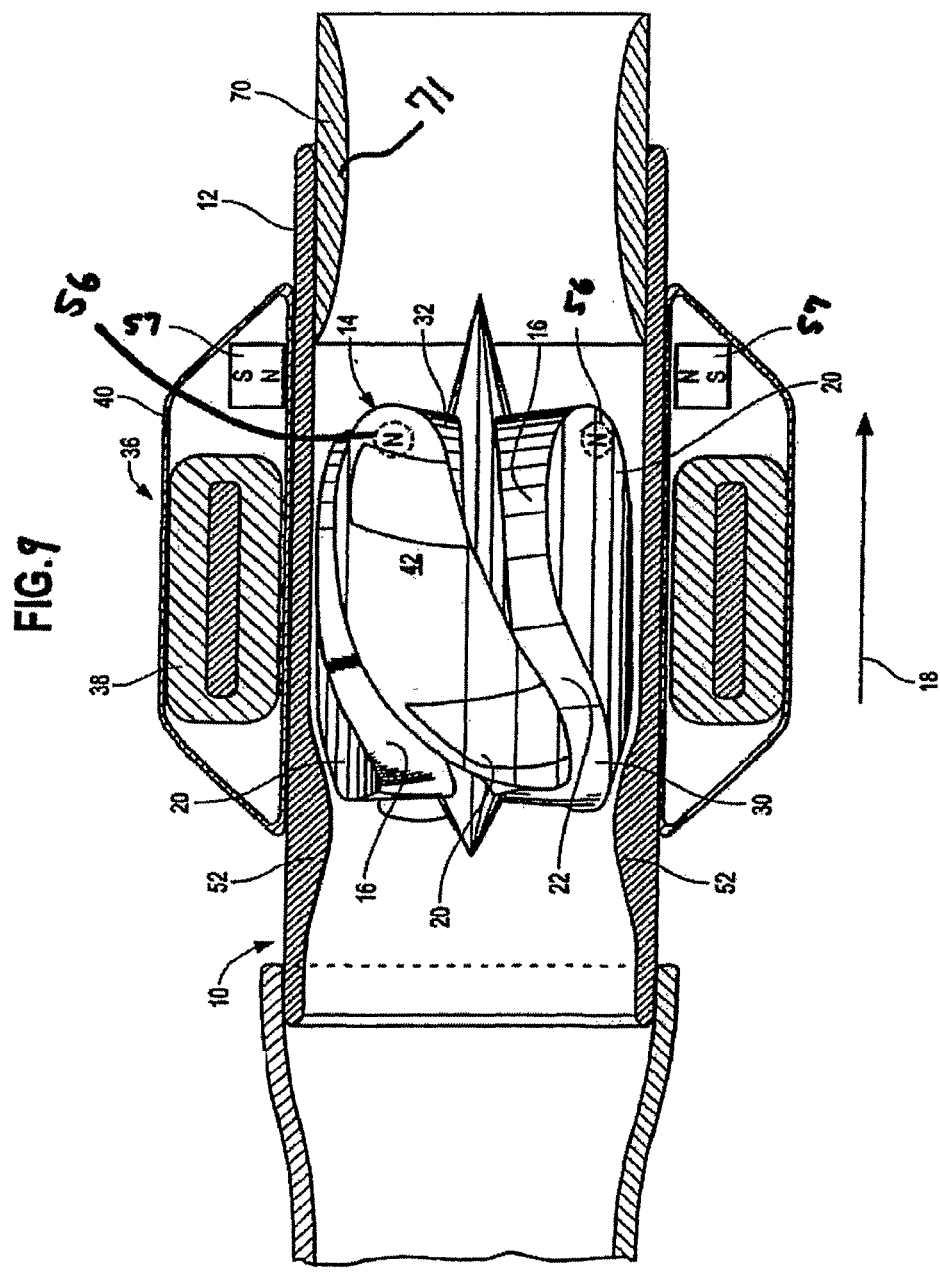

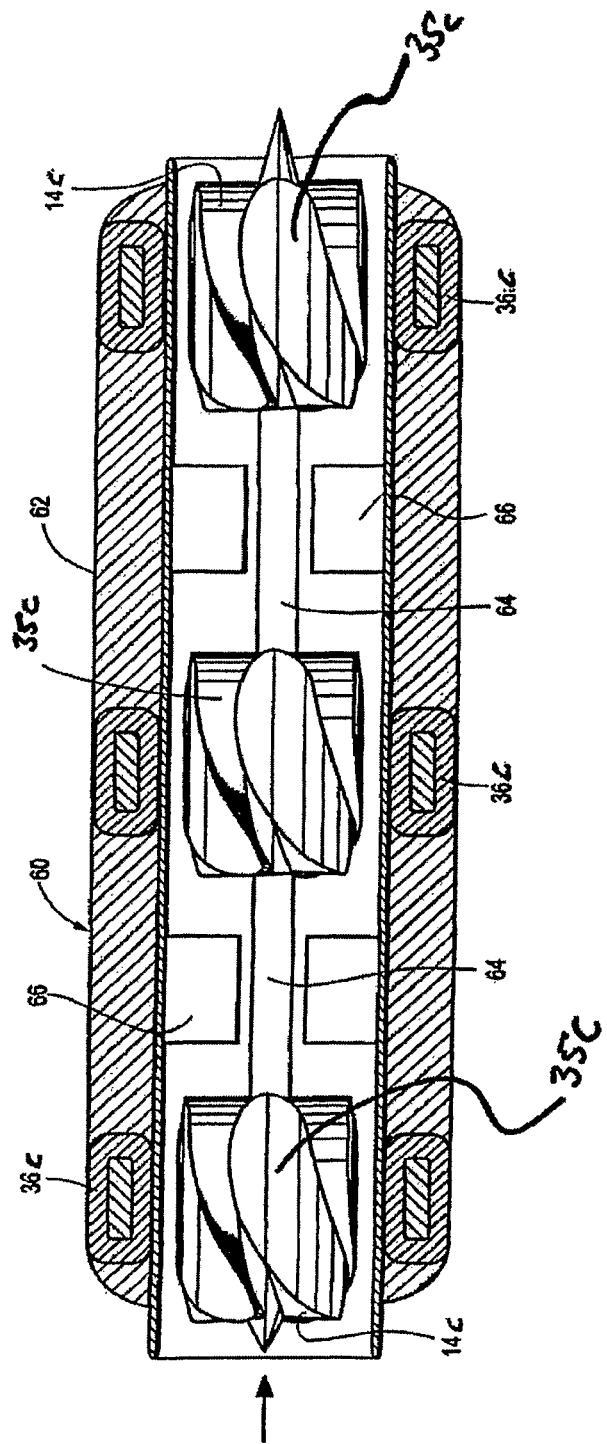

AXIAL FLOW PUMP WITH MULTI-GROOVED ROTOR

CROSS REFERENCE TO RELATED APPLICATIONS

The present application is a continuation of U.S. patent application Ser. No. 11/992,997, filed Sep. 29, 2009, now U.S. Pat. No. 8,790,236. U.S. patent application Ser. No. 11/992,997 is a national phase entry under 35 U.S.C. §371 of International Application No. PCT/US2006/021544, filed Jun. 2, 2006, published in English as WO2007/040663, which claims priority from International Application No. PCT/US2005/035964, filed Oct. 6, 2005, published as WO2006/118600, and to International Application No. PCT/US2005/042495, filed Nov. 22, 2005, published as WO2006/060260 and U.S. application Ser. No. 11/243,722, filed Oct. 5, 2005, now U.S. Pat. No. 8,419,609. The disclosures of all of said applications are hereby incorporated herein by reference.

FIELD OF THE INVENTION

The present disclosure relates to rotary pumps and, in particular, to axial flow blood pumps having a generally cylindrical rotor suspended within a corresponding cylindrical housing having a blood inlet at one end and blood outlet at another end, and motor components to provide rotational energy to spin the rotor and pump blood fluid longitudinally through the housing from the housing inlet to the housing outlet.

BACKGROUND OF THE INVENTION

The known axial flow pumps for blood have the advantage of narrow radial width, when compared with centrifugal flow pumps. They may therefore be used for intra-vascular or intra-heart blood pumping assistance. Axial flow pumps typically have a cylindrical housing with an inlet at one end, an outlet at the opposite end, and a rotor within the housing which has thin impeller blades or vanes attached to and protruding radially outwardly from the rotor. Thus, as the rotor rotates, the blades add work to the fluid, propelling the fluid through the housing from the housing inlet to the housing outlet.

A suspension system is provided to maintain the rotor in a desired position within the housing, and an electromagnetic motor is provided to spin the rotor. The rotor may be mechanically, magnetically or hydrodynamically suspended within the blood flow passage. A combination of such suspension techniques may be utilized.

Typically in the prior art, the rotor is suspended by mechanical bearings or bushings, some with a rotor shaft protruding through the pump housing to a motor drive mechanism. Magnetic suspension is also known, as in U.S. Pat. Nos. 6,368,083 and 5,840,070. The blood discharged from the pump, flows parallel to the axis of rotation of the rotor.

Axial blood flow pumps have heretofore used a thin blade design, with the motor magnets being placed either in the rotor shaft, relatively far away from the surrounding stator, as in pumps by Jarvik and Incor, or they use small magnets placed within the thin blades, as in a pump made by MicroMed. Both of these approaches tend to reduce the motor torque capacity and efficiency, and they require mechanical rotor support involving abutting surfaces that move and wear against each other in rotation.

It is desirable for blood pumps, whether internally or externally located, to be more tolerant of flow variations than the previous thin blade designs and to exhibit low hemolysis, good resistance to thrombosis, adequate system efficiency, and very high reliability for the expected duration of use for the device. Internally located blood pumps are also subject to anatomical Compatibility design constraints and the need for elimination of mechanical wear and associated failure modes in order to provide successful, long-term, implantable devices.

While the pump of this invention is described in terms of a blood pump, it is also contemplated that the pump might be used for pumping chemically difficult fluids or non-magnetic fluids, where a sealless design is highly desirable, and the fluid must be gently handled for various reasons, for example because it is unstable to mechanical stress, causing decomposition and even explosiveness, or because it is another complex, biological fluid besides blood, having critical stability parameters.

SUMMARY OF THE INVENTION

In accordance with the present invention an axial flow sealless and wearless blood pump is provided which comprises a tubular pump housing having a blood inlet at one open end and a blood outlet at the other open end opposite the inlet. A cylindrical rotor is suspended within the housing tube. The rotor comprises a plurality of peripheral and radial surfaces to engage and create pressure to assist in movement of the blood through the housing from the inlet end to the outlet end. A motor is provided to cause the rotor to spin within the housing. In one embodiment, the motor stator includes electrically conductive coils located external to or within the housing tube. A plurality of magnetic motor drive poles is provided on the rotor, spaced about its peripheral surfaces. The stator coil provides magnetic flux to cause the rotor to spin.

The rotor comprises a cylindrical body having a leading edge portion for engaging blood entering the housing at the inlet and a trailing edge portion for enhancing the discharge of the blood at the outlet of the housing. The rotor comprises one or more grooves each extending from an entry channel at the leading edge portion of the rotor to an exit channel at the trailing edge portion so as to define a plurality of arcuate peripheral land areas therebetween on the surface of the rotor. The sidewall surfaces defining each groove extend radially to the rotor surface but are not necessarily parallel to each other. In some embodiments each groove has a central portion defining a flow channel curved at least partially around the rotational axis of the rotor and in fluid flow communication with a substantially axially directed channel at the trailing edge portion of the rotor. The sidewalls of the grooves add axial thrust to the blood when the rotor is spinning and impart a rotational momentum to the flow of blood downstream of the rotor. In some embodiments, the central portion of each groove defines a narrower flow channel than is provided at its entry and exit channels. In some embodiments each groove is wider at its exit channel than at its entry channel to enhance the exit flow characteristics of the blood. In one embodiment, the combined total width of the central portions of the groove flow channels is substantially equal to or less than the collective, total arcuate widths of the peripheral land areas formed between the groove flow channels. The flow channels along the rotor may be helical along some portions of the rotor and generally axial directed along other portions of the rotor.

A plurality of hydrodynamic thrust bearing surfaces is provided on each of the peripheral surfaces of the land areas of the rotor. The bearing surfaces create fluid pressure at the periphery of the rotor thereby imparting radially symmetrical forces to the rotor, which maintain the radial position of the rotor within the housing when the rotor is spinning, and to provide good washing near the surrounding housing for increased resistance to thrombosis.

The land surface areas of the rotor between the flow channels of the grooves are each wider and longer at their peripheries than the thin blades of prior art axial flow blood pumps. This permits the emplacement or formation of relatively large motor drive magnets at or near the periphery of the rotor. Large drive magnets in the rotor increase magnetic force, and their placement at the rotor periphery reduces the gap between the magnetic poles of the rotor and magnetic flux generating coils of a motor stator. This arrangement improves motor torque capacity and electromagnetic efficiency of the pump. Axial magnetic stiffness provided by a motor of radial flux gap design may be used to assist in holding the rotor in its axial position within the housing.

A magnetic bearing system may be provided, as well as hydrodynamic thrust bearings, to help maintain the position of the rotor radially or axially within the tubular housing. Magnetic poles to assist in suspension of the rotor within the housing may be placed within the peripheral land surfaces between the grooves of the rotor to be attracted to or repelled by corresponding magnetic poles within or adjacent the surrounding pump housing.

In one embodiment, magnetic bearings may be used instead of hydrodynamic thrust bearings, to provide an all magnetic suspension system. Such magnetic bearings could be positioned or formed in the peripheral land areas of the rotor either forward or aft of the location of the motor drive magnets. Accordingly, a rotor in accordance with this invention does not require mechanical supporting structures upstream or downstream thereof. Hydrodynamic thrust bearings, with or without magnetic bearings, or exclusive magnetic bearings, will be sufficient to maintain the rotor in desired position during operation.

In some embodiments, the configuration of the tubular pump housing may include an annular sloped interior surface near the rotor's leading or trailing edge portions to provide a mechanical stop for axial movement of the rotor. Such a configuration provides additional axial support for the rotor, as may become necessary in the event of shock loading to ensure that the rotor remains in proper position within the housing. Alternately, a split housing configuration might be provided, with annular sloped surfaces at both the rotor leading and trailing edge portions, to provide radial support and axial support in both axial directions. The blood pump may also utilize one or more upstream and downstream flow straighteners or diffusers to enhance flow characteristics of blood as it enters or exits the pump.

A controller is provided to run the motor at a set rotational speed, which may be set, for example by the attending physician. Alternatively, the motor may be run at a rotational speed which varies in response to a physiological control algorithm.

Unlike axial flow pump designs heretofore using radial thin blade impellers, upstream and downstream struts or stator elements which may serve as flow straighteners or diffusers may be useful but are not required. The absence of these upstream and downstream flow straighteners permits a simpler mechanical design, with fewer axial tolerance concerns associated with their placement. Moreover, the absence of upstream flow straighteners or diffusers permits a pre-swirl to the upstream blood flow pattern that may serve to improve resistance to thrombosis.

In some embodiments, a volute may be used at the output end of the housing to improve the output flow characteristics of the blood. For example, a volute may be used to redirect the blood flow in a direction normal to the rotational axis of the pump. A volute may improve the output blood flow characteristics of an axial flow pump by converting rotational kinetic energy in the output flow from the axial flow pump to a slower output velocity having sufficient pressure for discharge into the vascular system.

The blood pump of this invention might be implanted within the vascular system or located within the chest cavity of a patient, such as the pericardial space, abdomen, or subcutaneously near the skin, in a manner similar to pacemaker implantation. Likewise, the pump may be kept external to the body for shorter term vascular circulatory support. Also multi-rotor or ganged rotor pumps having a plurality of axially aligned axial flow pumps of the type described herein could be used to provide single or bi-ventricular support, or even total circulation for the patient in the manner of a full, artificial heart. Moreover, such multi-stage pumps can be constructed with smaller diameter tubular housing for intravascular implantation.

BRIEF DESCRIPTION OF THE DRAWINGS

A more complete appreciation of the present invention and many of the attendant advantages thereof will be better understood by reference to the following detailed description when considered in connection with the accompanying drawings, wherein:

FIG. 2 is an elevational side view of a rotor of the rotary pump of FIG. 1.

FIGS. 3 and 4 are elevational views of two different sides of the rotor of FIG. 2.

FIG. 9 is a longitudinal sectional view of an alternate embodiment of the pump of FIG. 1.

FIG. 10 is a plan view, taken partially in longitudinal section, showing a multiple-rotor blood pump of the present invention.

DETAILED DESCRIPTION OF THE PREFERRED EMBODIMENTS

Figure 1:
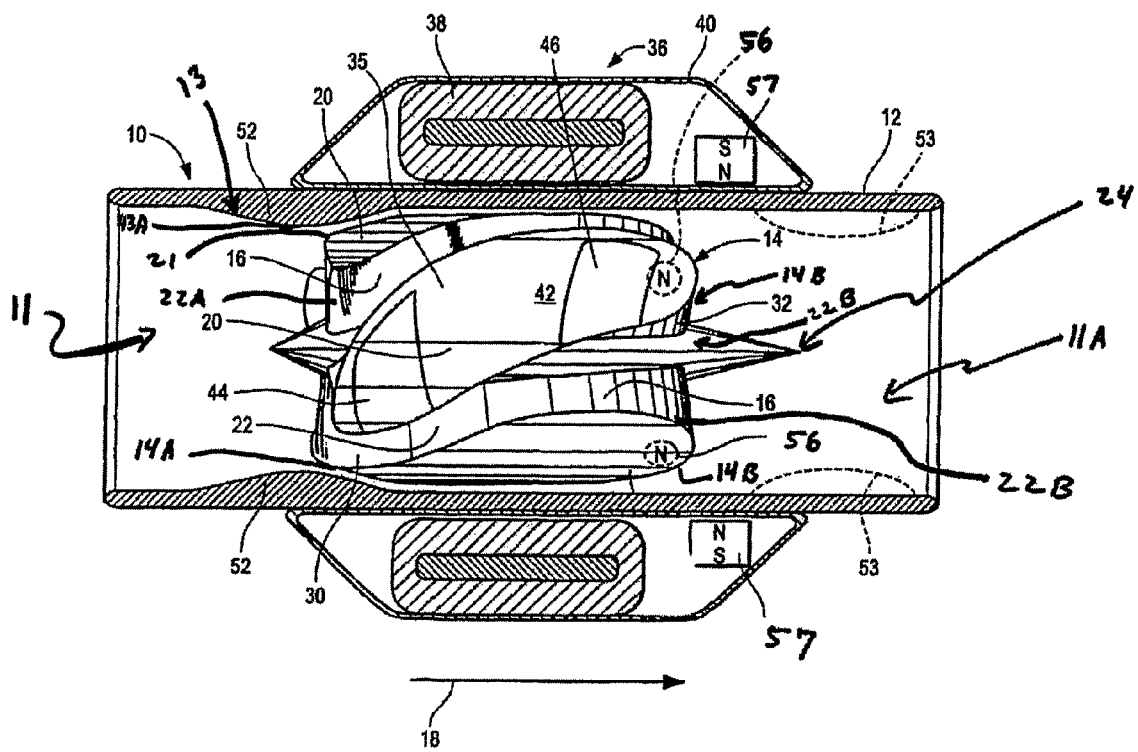
FIG. 1 is a longitudinal sectional view of an implantable, sealless, axial rotary blood pump in accordance with this invention.

In describing the preferred embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Referring now to the drawings and in particular to FIGS. 1-5, an embodiment of a blood pump 10 adapted to assist in pumping blood through a patient's vascular system is disclosed, comprising a hollow generally tubular pump housing 12. The pump housing 12 is non-magnetic and is made of a suitable biocompatible material such as titanium or a suitable ceramic material which is non-thrombogenic, rigid and exhibits minimum eddy current lossess. The housing 12 defines a blood inlet end 11 and a blood outlet end 11A so that blood flows through the housing in the direction shown by the arrow 18. In one embodiment the housing 12 has a constant exterior diameter while the inlet portion of its interior diameter first converges as indicated at 13 and thereafter diverges as at 13A to define an annular hump or ring, indicated in FIG. 1 by reference numeral 52.

A substantially cylindrical rotor 14 is positioned within the lumen of the pump housing 12, and acts as an impeller for pumping fluid within the housing. In one embodiment, the rotor 14 is provided with a tapered leading edge 14A which is contoured to follow the diverging portion 13A of the interior diameter of the housing. The converging and diverging diameter portions 13 and 13A may act as a mechanical stop to maintain the rotor 14 in proper axial position within the tubular housing if, for example, an external shock would tend to jolt the rotor out of its working axial position. In some embodiments the tapered leading edge 14A of the rotor may be provided with a hydrodynamic thrust bearing surface of the type described below to cooperate with the surface of the diverging diameter portion 13A of the housing 12 for additional protection against axial shock loading. The alignment between the housing diverging diameter portion 13A and the tapered leading edge 14A of the rotor could also be utilized to provide a magnetic axial preload at the rotor's leading edge, similar to that described below with respect to its trailing edge, to assist the rotor in maintaining its suspended and wearless position within the housing.

Rotor 14 comprises one or more grooves 22 each of which extends from an entry section or inlet channel 22A at the leading edge 14A to an exit section or outlet channel 22B at the trailing edge 14B of the rotor. The grooves 22 define fluid flow channels across the rotor. In some embodiments a plurality of grooves 22 formed in the rotor 14 are spaced apart and define a plurality of peripheral land areas 35 therebetween. Each groove is defined by a pair of side walls 16 extending substantially radially to the rotational axis of the rotor, but not necessarily parallel to each other.

As shown in FIGS. 1-4 and 6, each of the grooves 22 has a central flow channel 30 that curves at least partially around the rotational axis of the rotor and opens into a substantially axially extending outlet channel 22B. The curved central portion 30 is narrower than the inlet channel 22A or outlet channel 22B. The relatively wide outlet channel and its axial orientation enhances the discharge flow characteristics of the blood being pumped by more easily allowing for the release of blood from the rotor. The grooves 22 and their side walls 16 tend to drive blood in the axial direction, shown by the arrow 18, as the rotor 14 is rotated (clockwise in the embodiment of FIG. 1).

Figure 5:
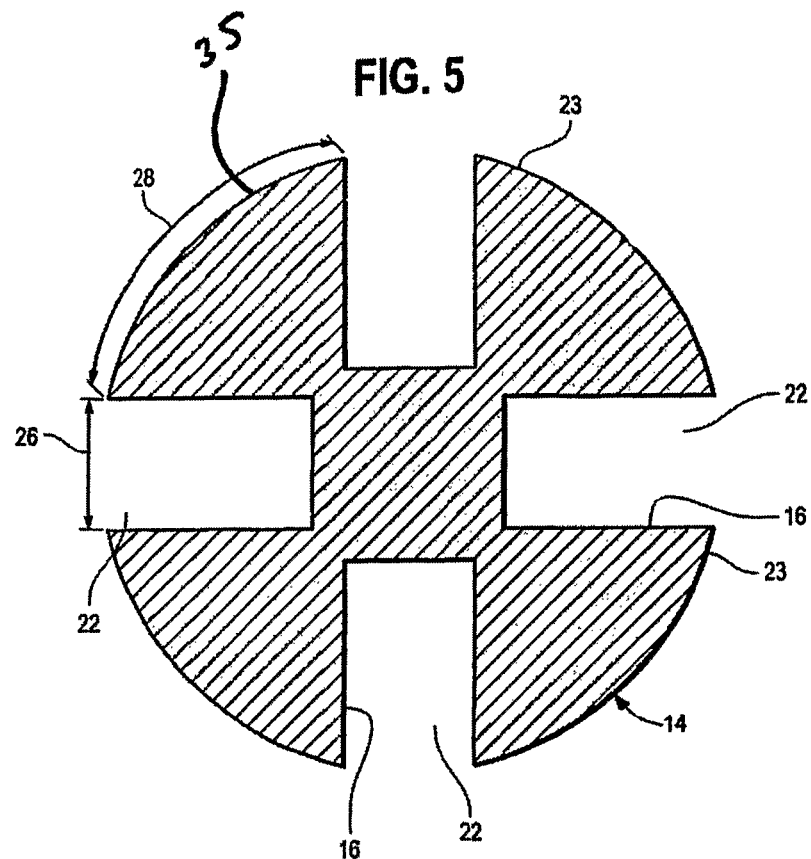
FIG. 5 is a sectional view taken along line 5-5 of FIG. 2, with internal parts omitted.

In one embodiment, the number of grooves 22 may be in the range of from 2 to 8, with four being typical. Irrespective of the number of grooves, their collective widths at the outer periphery 23 of the rotor 14 (FIG. 5) is equal to or substantially less than the collective, total circumferential width at the same outer periphery 23 of all of the land areas 35 defined between the grooves. By way of example, as shown in the embodiment of FIG. 5, the peripheral width of a groove 22 at the cross section of the rotor taken along the line 5-5 of FIG. 2 is shown by the arrow 26. The arrow 26 is shorter than the width of an adjacent land section 35 as measured by the length of the arc 28. Collectively, at the central portions along the grooves 22, the total width of the grooves 22 is less than or equal to the collective, total width of the respective land areas 35.

In this embodiment, the depth of each of the grooves 22 is greater than the radial extent of the blades in comparable and conventional thin blade axial pump designs. For example, for heart pump uses, the average depth of the grooves 22 from their outer perimeters may fall within the range of from 1 mm to 5 mm. In some embodiments the average depth of the grooves is approximately ⅓ the diameter of the rotor, but is less than the radius of the rotor. In other embodiments the grooves may be deeper at the entry channel 22A at the leading edge of the rotor and shallower at the exit channel 22B at the trailing edge of the rotor.

With reference to FIG. 2, the blood pump 10 further comprises a rotor, which includes a plurality of relatively large permanent drive magnets 34 (shown in dotted lines) formed within each of the wide land areas 35 of the rotor 14. According to one embodiment of the present invention, the permanent drive magnets 34 in the rotor may be produced by magnetizing selected portions of the peripheries of the land areas 35. This may be accomplished, for example, by constructing the rotor from a magnetic alloy, which may be isotropic, and magnetizing desired peripheral sections to form a plurality of magnetic poles with various geometric orientations. It is preferable to use a magnetic alloy that is biocompatible so that no additional coating is required. Such a rotor may be easier and less expensive to manufacture than impellers formed from multiple parts.

With reference to FIG. 1, the motor also comprises a motor stator 36 having electrically conductive coils 38. The coils are placed within an enclosure 40 which surrounds the tubular housing 12 and the rotor 14. The motor stator 36 serves to rotate rotor 14 by the conventional application of electric power to the coils 38 to create magnetic flux. The permanent drive magnets incorporated into the wide land areas 35 of the rotor are selected for magnetic properties, length, and cross-sectional area in order to provide good electromagnetic coupling with the magnetic flux created by the motor stator. Because of the relatively large surface area of the land areas, the nature and placement of the rotor magnets becomes relatively easy to effect. This arrangement provides strong electromagnetic coupling and the necessary magnetic axial stiffness to maintain the rotor in position. In one embodiment, the magnetic coupling between the stator flux and the drive magnets in the rotor creates torque, causing the rotor 14 to rotate clockwise. It will be understood by those skilled in the art that the rotor could be caused to rotate in a counterclockwise direction without departing from the scope of the invention.

The motor may be a three phase, brushless DC motor. In one embodiment the motor could be a toroidal, three phase and wye connected design. The stator may have a back iron design which is consistent with a typical radial flux gap motor. If desired, the motor stator can comprise a separate, hermetically sealed enclosure 40 that slides over the tubular housing 12 into position. A braised weld ring to the enclosure 40 outer surface may be used to secure the motor stator housing in position. Laser welding is one possibility for securing the motor stator enclosure 40 to the housing and obtaining a hermetic seal. The specific technology for accomplishing this known in the prior art.

Figure 6:
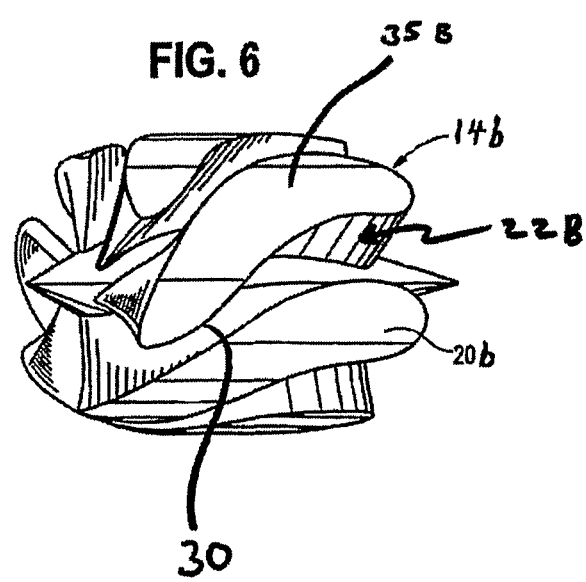
FIG. 6 is a perspective view of an alternative embodiment of a rotor usable in the pump of this invention.

Referring to FIG. 6, another embodiment of a rotor 14b for the blood pump of this invention is disclosed. Rotor 14b is shown to have six peripheral land sections 35b between the flow channels 22 having central portions 30. Otherwise, the nature and configuration of the rotor 14b is similar to the rotor of the other embodiments disclosed herein.

Figure 7:
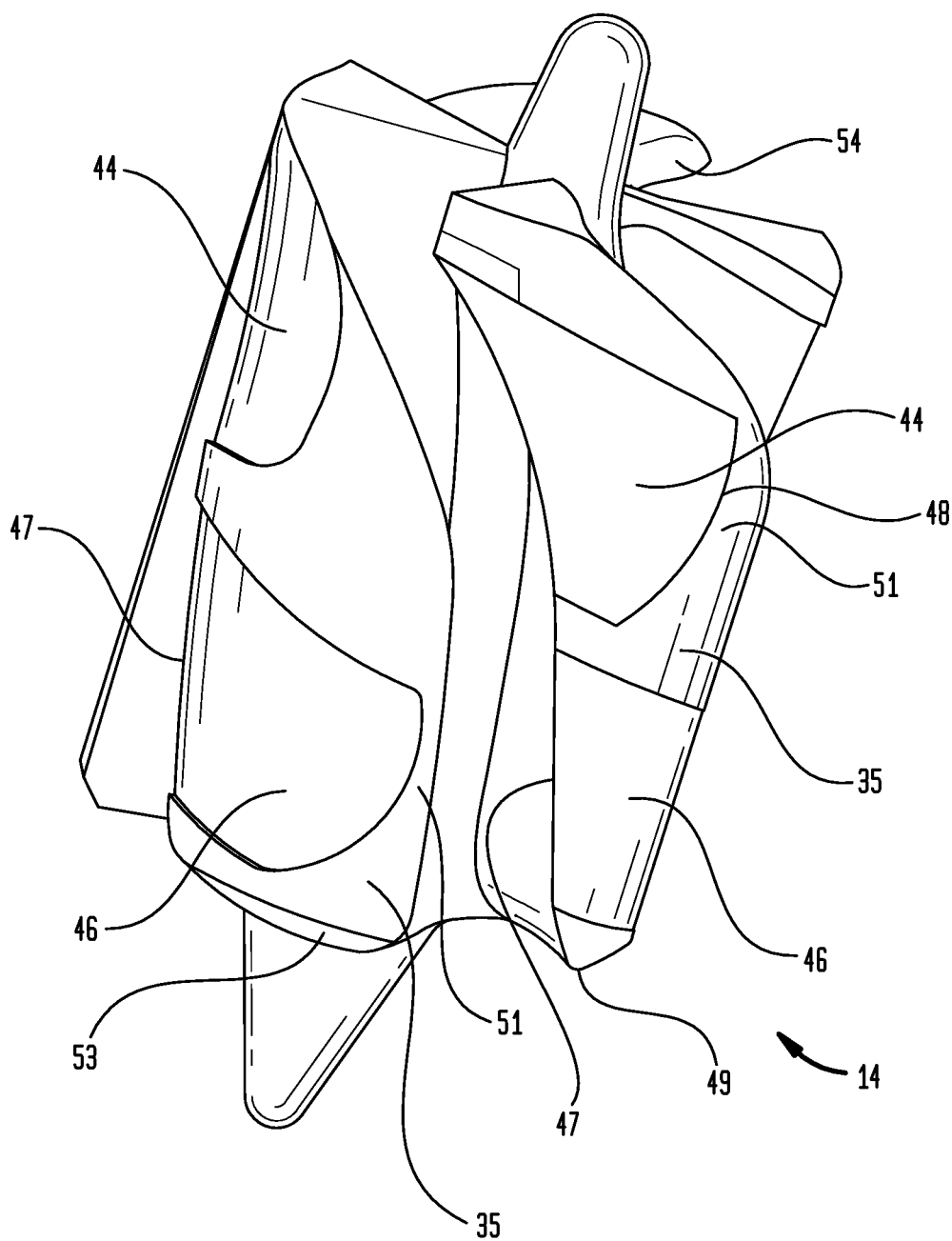
FIG. 7 is a rear perspective view of a rotor of the embodiment of FIG. 1.
Figure 8:
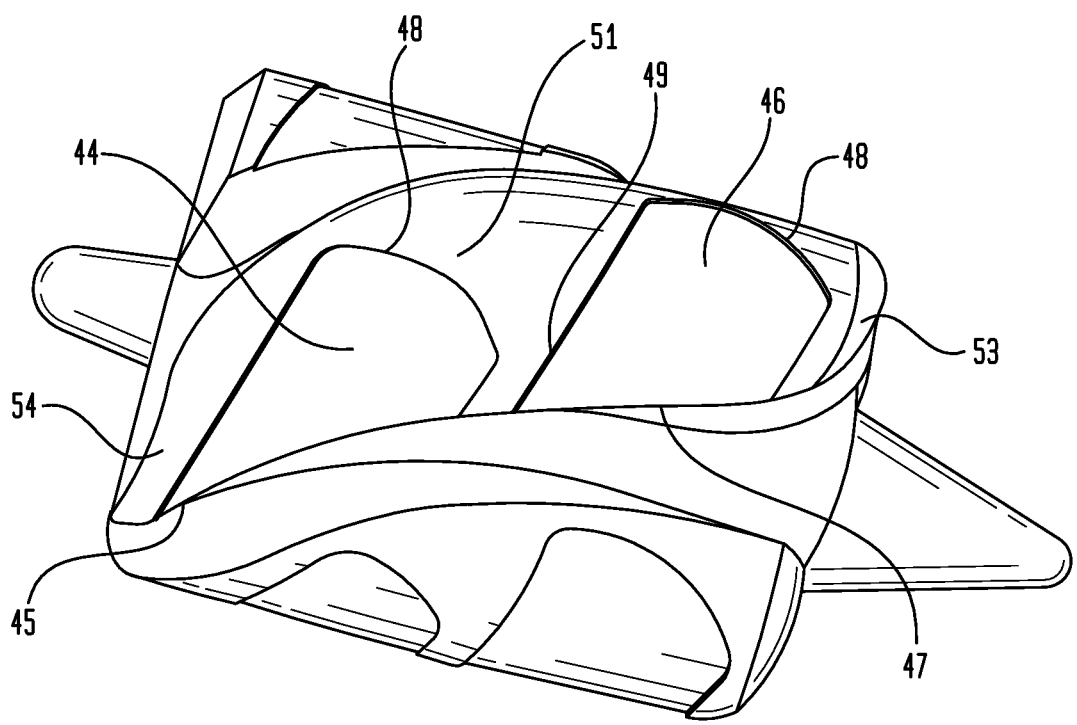
FIG. 8 is a top perspective view of the rotor of FIG. 7.
Figure 8A:
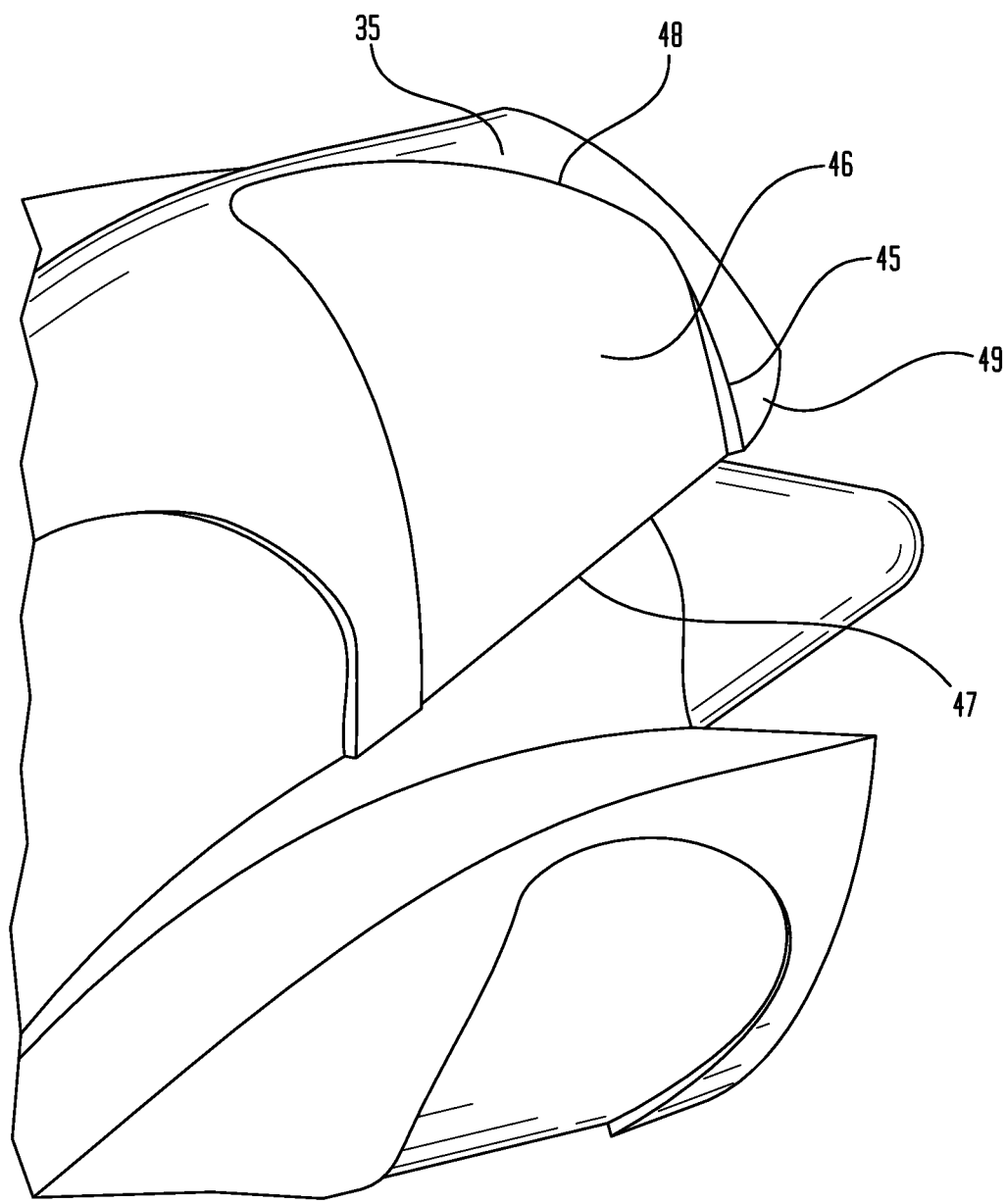
FIG. 8A is an enlarged, fragmentary, perspective view of a portion of the rotor of FIG. 7.

Referring to FIGS. 7, 8, and 8A, there is depicted a rotor 14 which is similar to the rotor shown in the embodiment of FIGS. 1-5. The peripheral land areas 35 of the rotor 14 are each provided with one or more hydrodynamic thrust bearing surfaces 44 and 46. Each of the thrust bearing surfaces 44, 46 is disposed along the surface of the associated land area having a prescribed peripheral radius. The leading edge 47 of each of the bearing surfaces from the viewpoint of the (clockwise) spin of the rotor 14, is recessed by a predetermined amount below the surface of the associated land section, as depicted in FIGS. 8 and 8A by reference numeral 45. The recessed surface then tapers in a gradual, curved manner across the land area along an arc, the axis of curvature of which is not necessarily co-axial with the rotational axis of the rotor. The tapered bearing surface terminates at a rear end 48, at which point each bearing surface 44, 46 is feathered into the periphery of the land area with a smooth transition and is no longer recessed with respect to the continuing downstream surface of the land area.

As the rotor rotates, the respective thrust bearings, 44, 46 on each land area 35 scoop blood onto the bearing surfaces whereby it flows between the bearing surfaces and the inner wall of the tubular pump housing. The effect of the tapered configuration of the thrust bearing surfaces is to force blood to flow through a decreasing or constricting area created between the bearing surfaces and the inner wall of the tubular pump housing. This results in increasing fluid pressure upstream within the constriction, which pressure acts against the bearing surface areas and produces a net symmetrical force for radial support of the spinning rotor. That hydrodynamic thrust bearings act in this way to cause radial pressure on a rotor is well known to the art generally, as in U.S. Pat. No. 5,840,070. The hydrodynamic force that is thus created on the surfaces of the rotor land areas tends to hold the rotor suspended and centered within the lumen of the tubular housing 12 in a manner shown in FIG. 1, and resists dynamic, radial shock loading forces without the need for physically contacting bearing surfaces. The thrust bearing surfaces 44 and 46 may be formed directly into the peripheral surfaces of the land areas 35 or may be placed within suitable cavities formed in the outer peripheral surfaces of the land areas and held in place by a suitable cover.

In some embodiments, hydrodynamic thrust bearing surfaces are created on the leading or trailing edge portions of the rotor. For example, with reference to FIGS. 1-3, the surface area 20 at the leading edge 14A of the rotor is tapered into a suitable thrust bearing configuration to cooperate with the diverging interior surface 13A of the tubular pump housing. Such a thrust bearing would resist longitudinal movement of the rotor to the left, as shown in FIG. 1. Alternatively, the diverging portions 13A partially defining the annular ring 52 may, if desired, comprise hydrodynamic thrust bearings cooperating with the adjacent rotor surface to prevent contact between the rotor 14 and the ring 52 as the rotor operates in a clockwise rotation.

Hydrodynamic thrust bearing surfaces may also be located on the rotor near its trailing edge 14B, in which event the inner diameter of the tubular pump housing near its outlet end 11A would be constricted as shown in dotted lines in FIG. 1 to define an annular ring 53 similar to the ring 52 near the inlet end 11. Such thrust bearings on the rotor or formed on a side of the ring 53 would serve the similar purpose of replacing or of supplementing the repulsive magnetic poles of magnets 56 and 57 described below. Such thrust bearings may provide one or both of radial and axial support for the rotor and serve to increase the resistance to shock loading thereby improving rotor stability.

Hydrodynamic thrust bearings on the outer periphery of the rotor provide good surface washing. Centrifugal forces created by thrust bearings tend to push fluid toward the periphery of the housing interior, providing increased blood flow, which can improve the pump's resistance to thrombosis. In contrast, hydrodynamic bearings in the prior art which are closer to the axis of rotation have reduced surface washing, resulting in a greater possibility of blood coagulation. Thus, since by this invention, conditions are provided that reduce blood coagulation, a lower amount of anticoagulant may be used with the blood pump and patient, which may result in fewer patient adverse side effects. If desired, hydrodynamic thrust bearing surfaces may be aligned in a helical fashion on the surfaces of the rotor to improve surface washing by the moving blood as the rotor spins.

As an alternative to hydrodynamic thrust bearings acting axially on the rotor, permanent rotor retaining magnets maybe placed in each land area 35 within the lead, trailing or both ends of the rotor. One or more corresponding permanent magnets may be placed within or on the tubular pump housing adjacent each rotor retaining magnet to effect repulsive magnetic forces acting to retain the axial alignment of the rotor within the housing. By way of example only, a permanent magnet 56 is shown in FIGS. 1 and 2 in dotted lines on a land surface area at the trailing end of the rotor 14. A corresponding permanent stator magnet 57 is emplaced within the enclosure 40 surrounding the tubular housing 12. The rotor magnet 56 may be formed by magnetizing suitable rotor material. If the north poles of the rotor magnet 56 and the stator magnet 57 are adjacent or face each other, as shown in FIG. 1, the repelling magnetic forces will assist in retaining the rotor in the proper axial position. Longitudinal or axial movement of the rotor to the right is thereby restricted by the repulsive action of magnets 56 and 57. Of course, magnetic south poles could be directed to face each other in similar manner, to achieve a generally similar effect. It will be understood that the magnet 57 may comprise a ring magnet or an electromagnetic coil.

With reference to FIG. 8A, in one embodiment, each of the thrust bearing surfaces is provided with shrouds 49 provided along each lateral side of a thrust bearing surface. These shrouds, defined by sidewalls of decreasing height created by the recessed portion of each bearing surface, reduce the amount of fluid leakage from the bearing surface, and allow the development of higher radial pressure levels. The reduction of such leakage to acceptable levels by means of such shrouds can almost double the load carrying capacity for the bearings.

An optional pressure relief surface downstream of each rotor thrust bearing surface may be provided to reduce hemolysis. This pressure relief surface consists of a portion of the peripheral land area that is contiguous with the rear end 48 of a thrust bearing surface and slightly diverges away from the housing wall. Blood passing over the thrust bearing surface is thereby directed across the pressure relief surface into an adjacent one of the grooves 22 formed in the rotor. Rounded surfaces 54 at the leading end of the rotor, seen in FIGS. 7 and 8, facilitate entry of blood into the flow channels of the rotor. Thus, an axial flow pump having wide peripheral land areas and utilizing shrouded hydrodynamic thrust bearings for radial or axial support is provided, having significant advantages over the known types of axial flow blood pumps.

In some embodiments, the rotor 14 may be produced by either machining, molding, or casting a single piece of ferromagnetic material, such as compression bonded neodymium or Alnico (aluminum-nickel alloy), or an alloy of about 70-80 percent by weight of platinum and about 20-30 percent by weight of cobalt. In some embodiments, from essentially 76-79 percent by weight of platinum is present in the alloy. In some embodiments, the alloy may contain essentially from 21-24 percent by weight of cobalt.

In one embodiment, an integral, one-piece rotor consists of essentially 77.6 percent by weight of platinum and 22.4 percent by weight of cobalt. Such a rotor is conventionally heat treated to achieve good magnetic properties, and may be magnetized, with North and South magnetic poles, as desired.

An advantage of such a rotor is that a single, integral piece made from the platimun and cobalt alloy can be easily fabricated into complex shapes, using conventional metal working and casting methods. Also, such an alloy is magnetically isotropic, so that parts can be easily magnetized with a plurality of magnetic poles in any geometric orientation. These characteristics allow the rotor to be fabricated from a solid piece of the alloy, thus eliminating the need to build assemblies of magnets and support structures, as in the case of prior art ventricular assistance devices, with a resulting reduction of manufacturing costs. Additionally, the alloy used in this invention is biocompatible, and has high resistance to corrosion, also having a Rockwell hardness on the order of 31 Rc, which eliminates the need for a hard, outer coating. It will be understood that the rotor material may be isotropic or anisotropic, as desired.

After fabrication, the rotor may be treated with a conformal, protective polymer coating of an organic polymer such as Parylene, or silicone, to prevent against oxidation by forming a hermetic seal around the rotor. On top of this, a hard, lubricious protective coating may be applied over the conformal polymer coating, to protect against wear and abrasion. Such coatings may include chromium nitride, titanium-nitride, or other commercially available coatings such as ME92, Med Co 2000, or DLC. Alternatively, as stated above, the use of a biocompatible magnetically isotropic alloy such as a platinum-cobalt alloy obviates the use of the protective coating. Designed for a permanent heart ventricular assist device, such a rotor could be a cylindrical device having a 10 millimeters outer diameter and 20 millimeters length, providing flow rates of 2-10 liters per minute against physiologic, differential blood pressures. Magnetization of the rotor land sections may occur before or after a coating application.

Figure 8B:
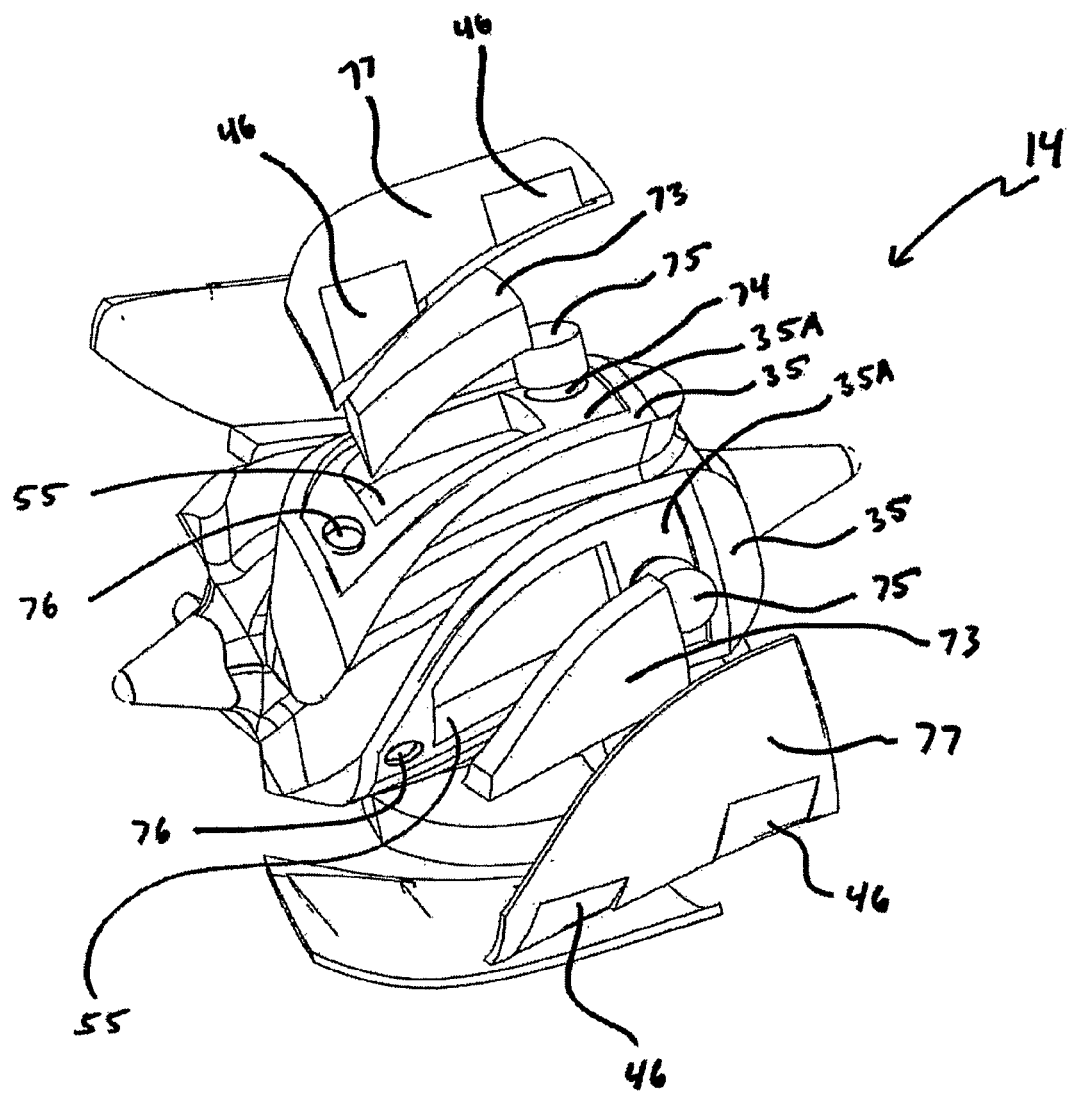
FIG. 8B is an exploded view of an embodiment of the rotor of FIG. 7.

With reference to FIG. 8B, an embodiment of the rotor 14 includes recesses 35A formed in each of the land areas 35, each of which recesses contains a cavity 55. Each cavity 55 is adapted to receive a discrete permanent drive magnet 73. The permanent drive magnets 73 serve the same purpose as the magnetized areas 34 described above in connection with FIG. 2. In this embodiment, the land area recesses 35A include cavities 74 adjacent each of the cavities 55. The cavities 74 are adapted to receive discrete permanent retaining magnets 75 which serve the function of the rotor retaining magnets 56 described above in connection with FIGS. 1 and 2. The land area recesses 35A also include bores 76 formed for the purpose of weight reduction and to achieve dynamic rotational balance in the rotor when desired. A contoured cover 77 is adapted to be inserted into each of the land area recesses 35A to retain the discrete drive magnets 73 and retaining magnets 75 in position on the rotor. In this embodiment the covers 77 contain the hydrodynamic thrust bearing surfaces 44 and 46 for the rotor described above in connection with FIGS. 7, 8 and 8A.

Referring to FIG. 9, there is disclosed an embodiment of the pump of FIG. 1 having a sleeve 70 inserted within the outlet of the housing 12 and having a reduced internal diameter area 71. The reduced internal diameter area 71 serves as a stop to mechanically retain the rotor 14 against movement in one axial direction, to the right in FIG. 9, so that magnets 56 and 57 may be unnecessary. In addition, the reduced internal diameter configuration of the sleeve 70 renders this arrangement suitable as a pediatric version of the axial flow pump of this invention as it will result in a reduced flow rate compared to an unsleaved configuration.

Referring to FIG. 10, a ganged series of axial flow blood pumps 60 has a common, cylindrical housing 62 in which a plurality of rotors 14c are mounted on a common shaft 64 in spaced-apart axial relationship. In one such embodiment, the rotors are commonly driven by the shaft 64 to rotate as one. Such a device is described in co-pending application Ser. No. 11/118,551, the content of which is incorporated herein by reference. Each of the rotors 14c has peripheral land areas 35c, similar to the land areas 35 of the previous embodiments. By this means, added pumping power can be provided in the form of a multiple stage pump, with the rotors in series connection. Accordingly, a high capacity pump of smaller diameter can be provided.

Motor stators 36c, comprising electrically conductive coils are provided, one for each rotor, so that each of the respective rotors performs in a manner similar to that of the rotors described for previous embodiments, but for their connection with the common shaft. The rotors 14c and stators 36c may be of the same design as any of the previous embodiments, however, each rotor need not have the same number of grooves or land sections between the grooves.

Stator blades 66 of traditional thin blade design may be mounted to extend radially inwardly from the inner wall of pump housing 62 downstream of at least two of the three ganged rotors, although such blades are not normally required in the axial flow pumps of the present invention. The stator blades 66 serve to diminish the rotational momentum of the axial flow output from the rotors before the flow encounters the next rotor. This arrangement permits more hydraulic work to be added to the blood or other fluid. Any desired number of these generally radially extending blades 66 may be provided, if desired. Moreover, if desired, the leading or trailing end of each of the stator blades 66 may be provided with suitable hydrodynamic thrust bearing surfaces to provide additional axial support to the rotor. The stator blades 66 may also include integral permanent magnets to define magnetic bearings to support the rotor. Permanent magnets mounted in or on the appropriate leading or trailing ends of each rotor can provide repulsive magnet poles to assist in the axial stability of the rotors.

In the embodiment shown in FIG. 10, each of the motor stators 36c is axially aligned with its corresponding rotor. Such alignment may be altered to accommodate magnetic coupling or magnetic repulsion to provide extra axial magnetic support.

Figure 10A:
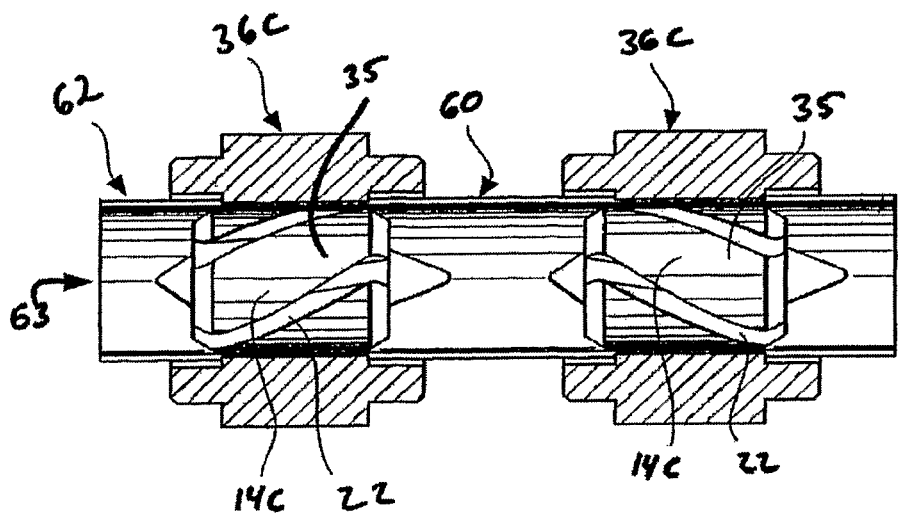
FIG. 10A is a plan view of another embodiment of the blood pump of FIG. 10.

Referring to FIG. 10A an alternative multi-rotor axial pump consists of a plurality of blood pumps 60 each of which has one of the pump rotors 14c having the characteristics of the rotors 14 described above. The rotors 14c are axially aligned in spaced-apart relationship and adapted to pump blood or other fluid consecutively through the common cylindrical housing 62 made of biocompatible material that exhibits minimum eddy current losses, as described above in connection with single rotor pumps. In this embodiment, the individual rotors 14c function independently without a connecting shaft. Motor stators 36c each comprise an electrically conductive coil as in the previous embodiments, one for each rotor, so that the respective rotors perform in a manner similar to that of the previous embodiments. The stators 36c also may be of a design as previously described. The multiple rotors 14c acting in concert provide added pumping power and therefore enables a high capacity pump of smaller diameter than a single stage pump, and may be adapted for implant directly into the vascular system of a patient and otherwise reduce patent trauma.

In one embodiment, the independently rotatable rotors 14c rotate at the same rate. It will be understood that the rates of rotation of the multiple rotors may vary, one from the other, as desired. In some embodiments, one rotor may rotate clockwise, and be oriented such that its grooves tend to drive blood or other fluid through tubular housing 62 in the direction of arrow 63. An adjacent rotor may be oriented such that its grooves tend to drive blood in the same direction 63 upon counterclockwise rotation. Thus, the multiple rotors work together to drive fluid in direction 63, even while they rotate in opposite directions. An advantage of this arrangement is that a rotor rotating counterclockwise downstream from a clockwise rotating rotor tends to counteract the rotational momentum imparted to the pumped fluid by the upstream rotor. This permits more hydraulic work to be added to the fluid. Depending upon the power applied to the individual stators 36c, the respective rotors maybe driven at rotation rates which are similar, or different from each other, as may be desired. Adverse affects from misaligned motor drive waveforms are thereby reduced.

In some embodiments, the multi-rotor pump is free of stationary, swirl suppressing blades positioned within the housing and between the rotors. A need for such blades is diminished by counterrotating characteristics of the respective rotors.

In some embodiments, more than two rotors are present. Adjacent rotors will rotate in opposite directions from each other, so that clockwise rotating rotors are interspersed with counterclockwise rotating rotors in axially alignment within the pump housing.

A permanent ventricular assist device of multistage configuration as described above could have an outer diameter of six millimeters and a length of 15 millimeters, to provide flow rates of 2-8 liters per minute against physiological differential pressures, as previously described. Such a multi-stage pump could be used as a peripheral vessel blood insertion pump, operating outside of the body, or provide bi-ventricular support and even total artificial heart action. It will be understood, that the multiple rotors need not be ganged on a common shaft and that the motor stator for each rotor could be energized to effect clockwise or counterclockwise rotation of each rotor independently of the rotational spin of other adjacent rotors.

Figure 11:
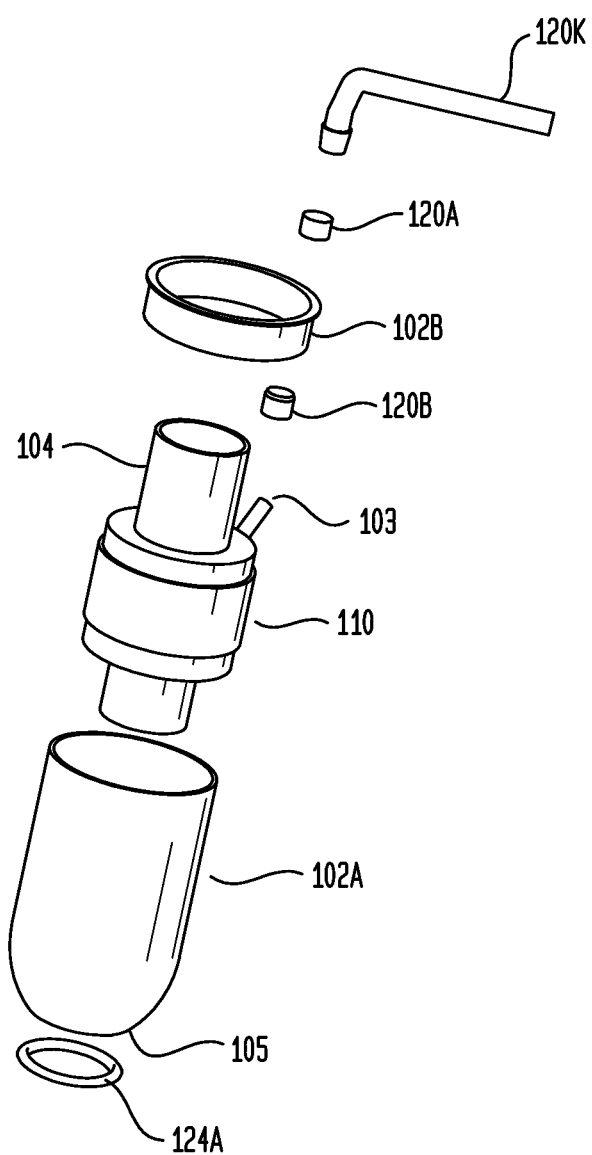
FIG. 11 is an exploded view of an alternate embodiment of the axial flow blood pump of the present invention.

FIG. 11 is an exploded view of an alternative blood pump configuration according to an embodiment of the present invention. The pump may comprise a primary outer cannula-like enclosure 102a and a secondary or discharge section 102b that fit together to seal a tubular housing 104 and a surrounding motor stator 110 in place within the assembled enclosure. An O-ring 124A may be used to prevent blood from leaking between the inner tubular housing 104 and the enclosure 102a. In this embodiment, the entire tubular housing and surrounding motor stator are enclosed with the cannula-like structure have an inlet opening 105 of reduced diameter, which provides a bullet-like configuration.

Figure 11A:
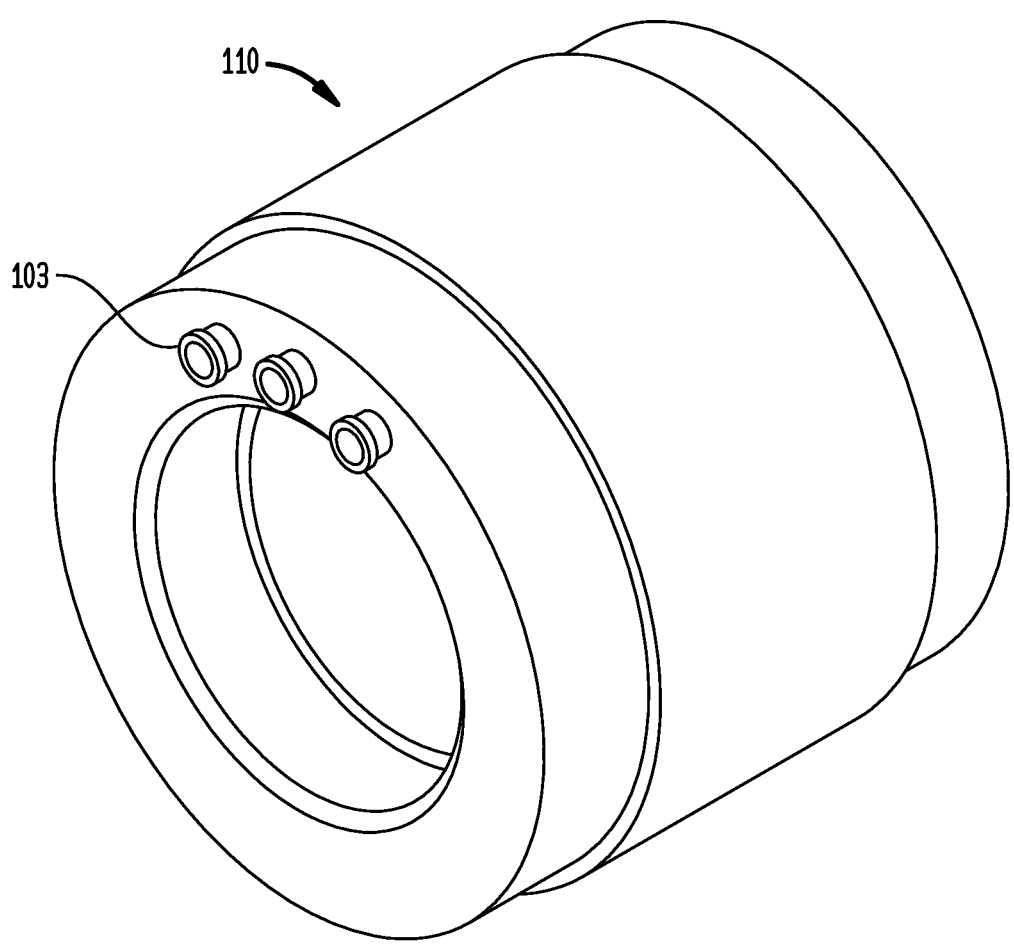
FIG. 11A is a perspective view of a motor stator of the embodiment of FIG. 11.

The motor stator 110 has three electrical cables 103 (seen best in the enlarged view of the motor stator in FIG. 11A) for three phase operation of the motor coils. The electrical cables may be contained within a suitable cable conduit comprising the three sections 120k 120a and 120b. It will be understood that other motor designs may be selected for applications requiring high speed communication or increased efficiency, without departing from the scope of the invention.

FIGS. 12-16 depict an embodiment of a blood pump in which the rotational kinetic energy of the axial flow of blood discharged by an axial flow pump is converted into a pressure flow at the outlet of the pump by a volute, indicated by reference numeral 106. While the incorporation of a volute is not necessary with the axial flow pump of the present invention, it is an optional embodiment for improving blood flow characteristics to further minimize thrombus formation and increase pressure of the pumped blood as it enters the vascular system.

Figure 12:
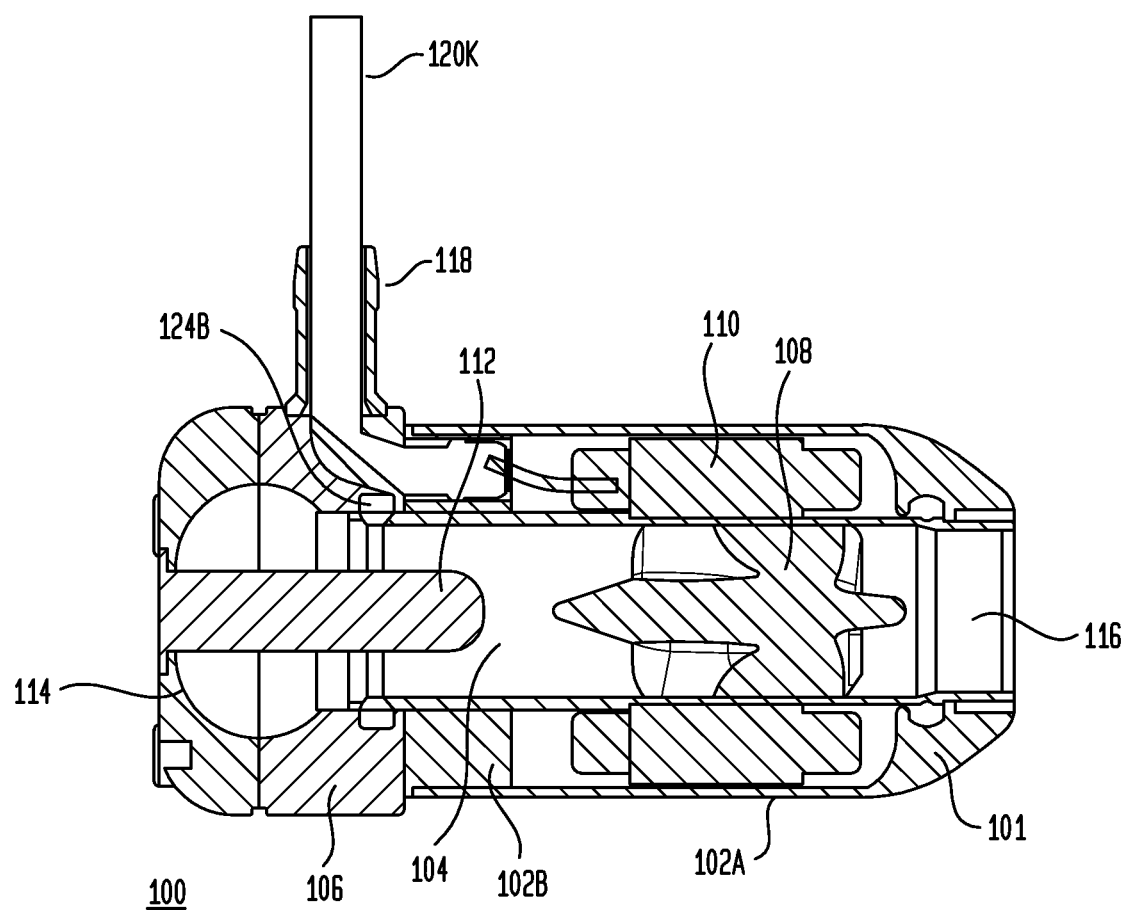
FIG. 12 is a schematic sectional view of a blood pump with a volute according to an embodiment of the present invention.
Figure 13:
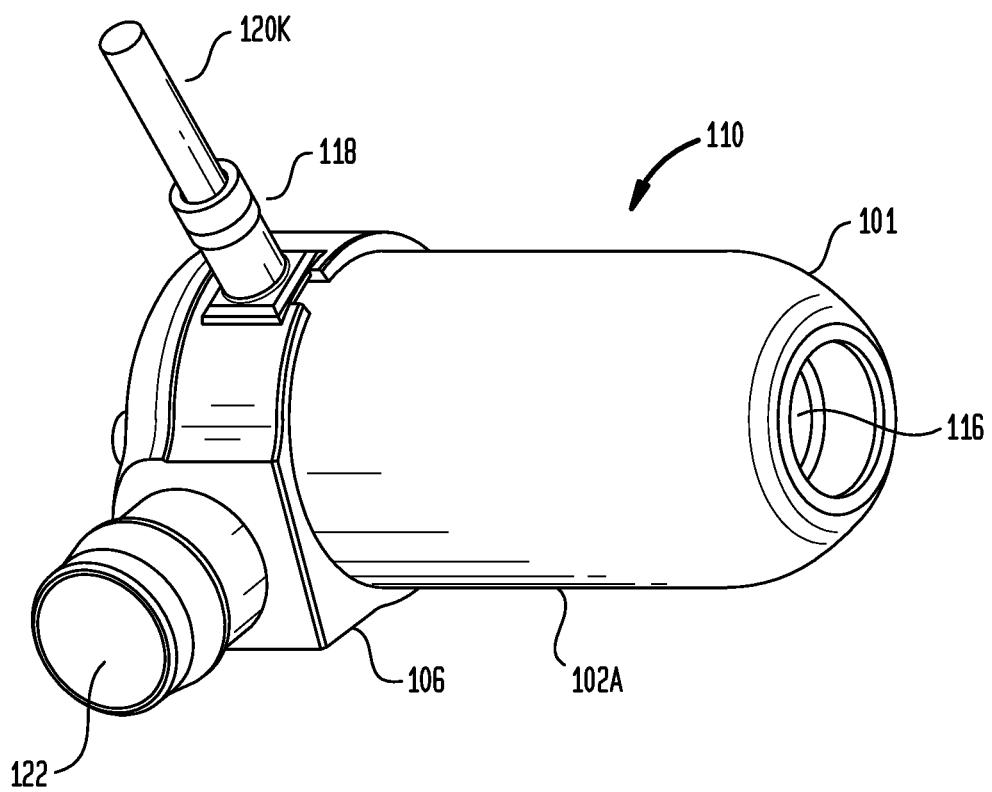
FIG. 13 is a perspective view of the blood pump with a volute shown in FIG. 12.

Referring to FIGS. 12 and 13, a blood pump 100 comprises a substantially cylindrical outer enclosure or cannula 102a. The cannula 102a may have the slightly rounded or bullet shaped front or inlet end 105 of reduced diameter having inlet 116 through which blood enters the pumping chamber. The pumping chamber is defined by the substantially tubular interior housing 104 having an external diameter smaller than the internal diameter of the cannula. The cannula 102a and tubular housing 104, as described above, may be made of a biocompatible non-magnetic material such as titanium or ceramic.

The motor stator ring 110 may be located on the outside the housing 104 and within the cannula 102a in the annular space formed between the housing 104 and the cannula 102a. The three phase control wires for the coils of the stator ring 110, described in detail above, are connected through the power and control cable conduit 120k that exits the pump through a port 118 which may be defined as part of the volute 106. A rotor 108, of the type described in detail above, may be magnetically or hydrodynamically suspended in operation within the housing 104 and centered within the stator ring 110 to provide an axial flow of the blood or fluid entering the inlet 116.

Figure 14:
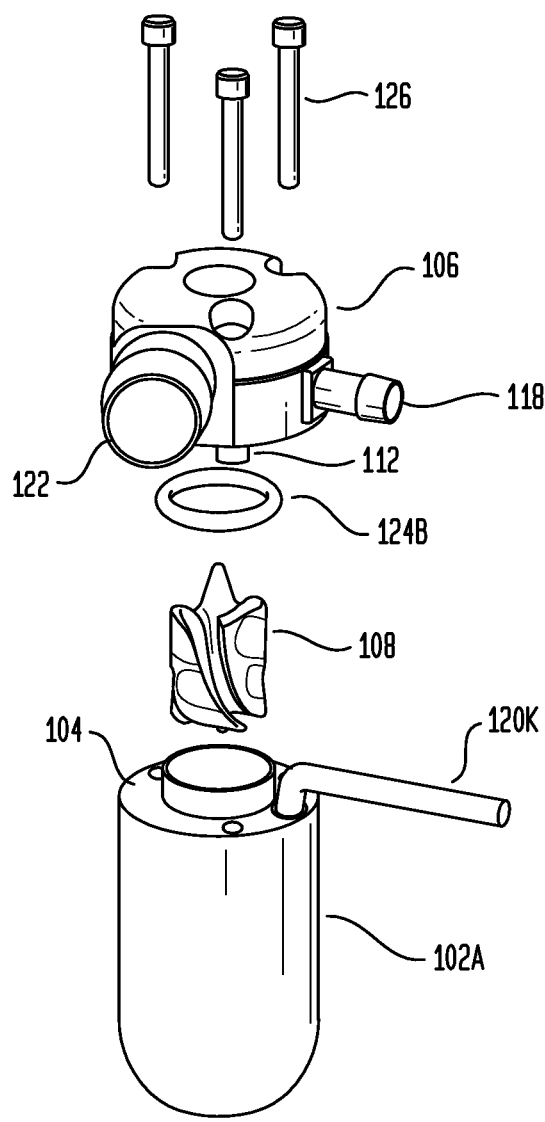
FIG. 14 is an exploded view of the blood pump with a volute shown in FIG. 12.

The volute 106 is sealed to the cannula 102a and the tubular housing 104 in a fluid-tight connection such that blood pumped by the rotor 108 is moved into a central chamber 114 (FIG. 12) of the volute 106. With reference to FIGS. 12 and 14, an O-ring 124B may be used to ensure a fluid-tight connection of the volute to the inner tubular housing 104. One or more screws 126 may be used to secure a hermatic connection.

Figure 15:
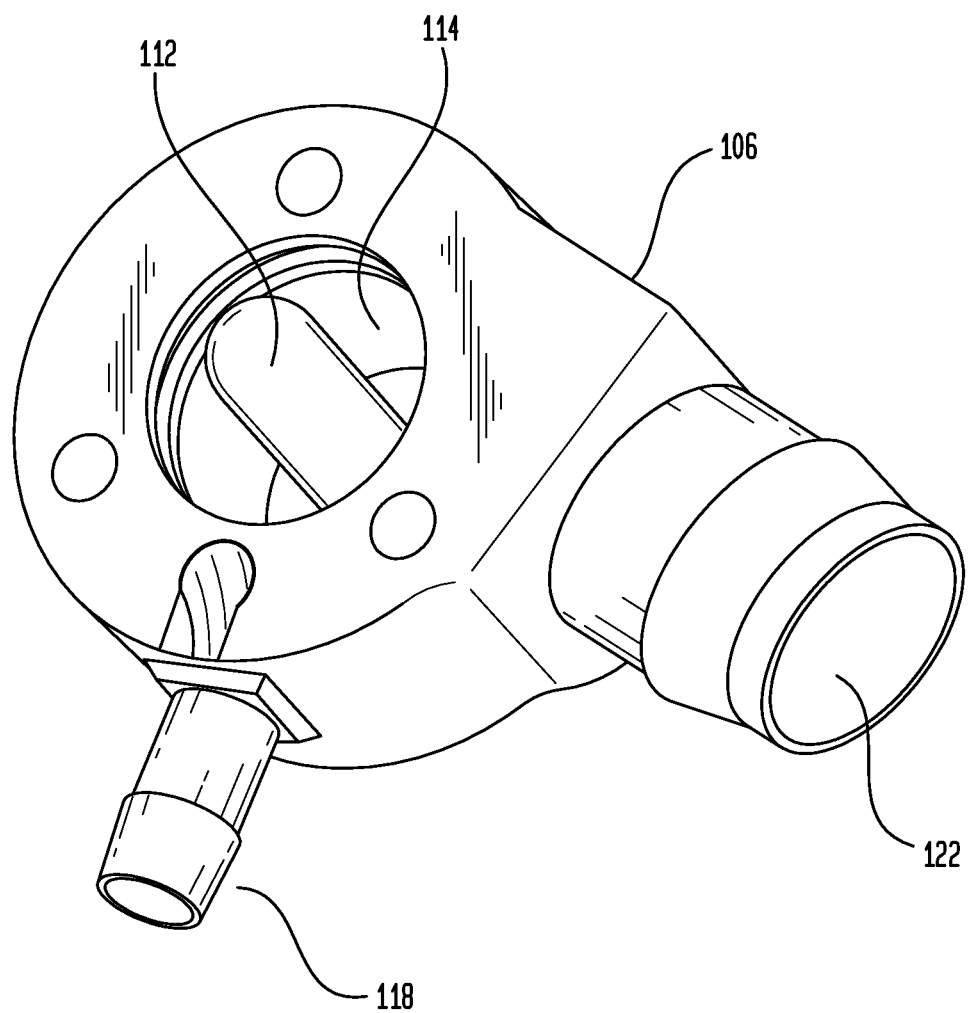
FIG. 15 is a perspective view of the interior of a volute according to one embodiment of the present invention.
Figure 16:
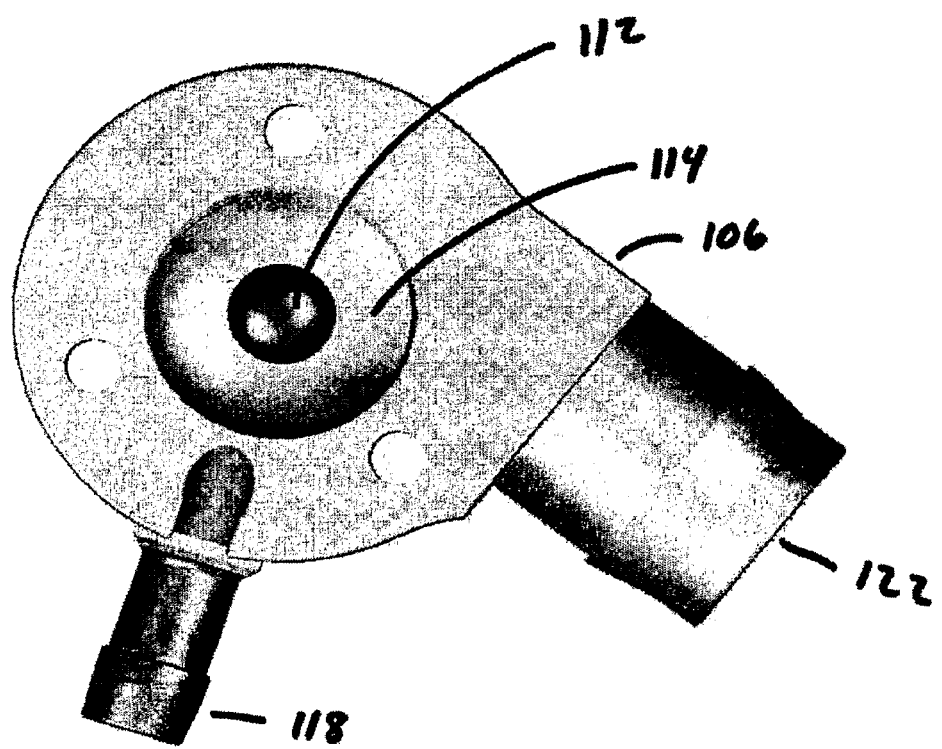
FIG. 16 is a top plan view of the interior of the volute shown in FIG. 15.

As depicted in FIGS. 15 and 16, the volute chamber 114 may be annular in cross section as defined by a downstream center post 112 projecting inwardly along the pump axis from the base of the volute along the rotational axis of the pump rotor 108. The center post 112 extends toward but does not contact the downstream end of the rotor 108, and may be a dome-topped cylinder (as shown in FIGS. 12, 14 and 15) or may be another shape that serves to affect the flow of blood discharged from the pump rotor, as described in detail below.

Blood driven by the rotor 108 and entering the volute chamber from the pump chamber of the axial flow pump has a rotational or spiraling momentum around the rotational axis of the rotor. The rotational momentum of the flow creates lower pressure areas in a central portion of the blood flow just downstream of the rotor. To some extent the lower pressure area is alleviated by a tapered axial extension 24 (FIG. 1) at the trailing edge 14B of the rotor. The center post 112 also tends to fill this lower pressure area in the downstream rotational blood flow characteristics as the blood enters the chamber 114 of the volute. Blood thereafter fills the annular chamber 114 of the volute and the fluid pressure of the system causes the blood stream to flow in a substantially centrifugal direction through the chamber 114 to the volute discharge or outlet 122, depicted in FIGS. 13-16, thereby establishing the output pressure. In this embodiment, the volute is bladeless and the discharge blood flow is in accord with the longitudinal nature of the blood flow within the vascular system. Typically, a blood pump of this embodiment will be implanted such that the cannula portion traverses the apex of a heart ventricle, while the volute portion remains outside of the heart. A graft (not shown) is used to connect the discharge or outlet of the volute to an artery of the vascular system of the patient.

Figure 17:
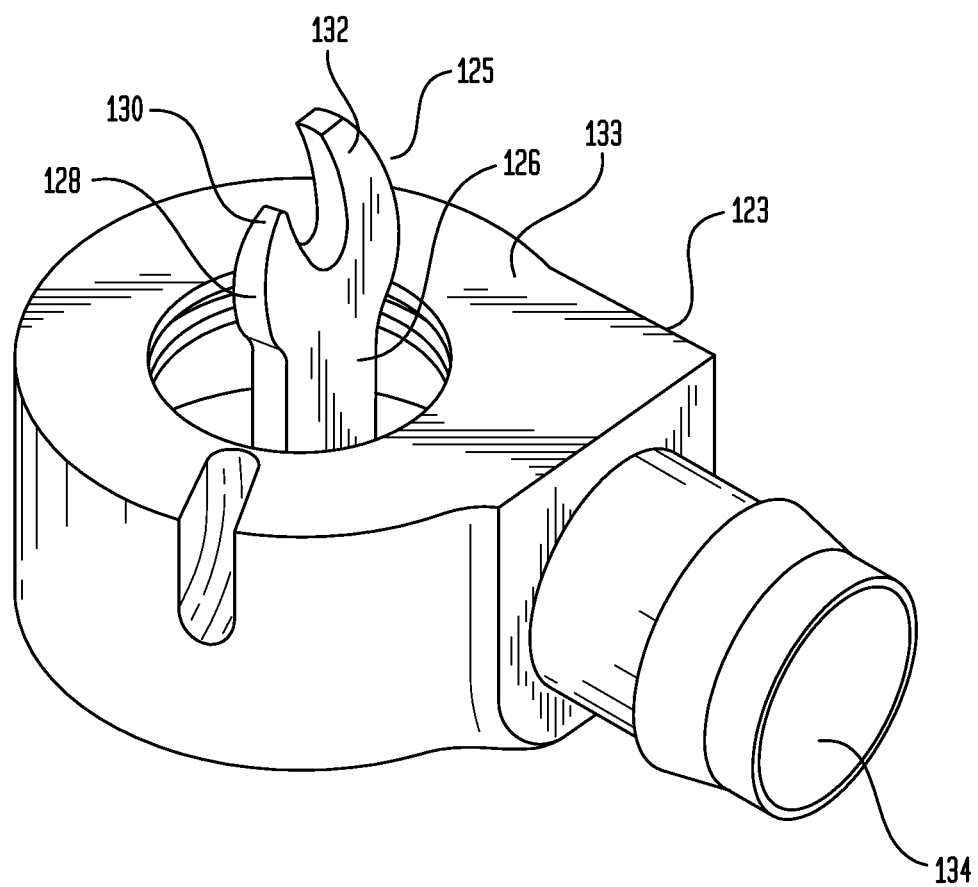
FIG. 17 is a perspective view of the interior of a volute according to another embodiment of the present invention.

Referring now to FIG. 17, there is depicted an embodiment of a centrifugal volute 123 with an alternate configuration for a flow straightner adapted to extend generally axially into the pump chamber of an associated axial flow pump. In this embodiment, the volute 123 has a flow chamber 133 of generally circular cross section from which extends a dual legged stator element 125 projecting out of the volute chamber and inwardly with respect to and along the axis of an axial pumping chamber as described above (not shown). The stator element has a pair of parallel legs 126 and 128 extending substantially co-axially with the rotational axis of the pump. The inner end portions of each of the supporting legs 126 and 128 are bent or curved such that the end portion 130 of the leg 128 is curved to project at an angle of about 45° to the longitudinal axis of the stator element 125 and the axis of an associated pumping chamber. The inner end portion 132 of the support leg 126 is also curved to project at angle of 45° to the pump axis. The axis of curvature of the end portion 130 is perpendicular to the axis of curvature of the end portion 132. The dual legged stator 125 acts to change the kinetic rotational momentum of the blood flow output from the axial pump to a pressure flow as the blood enters the centrifugal chamber 133 of the volute 123 before discharge through radial outlet 134.

Figure 18:
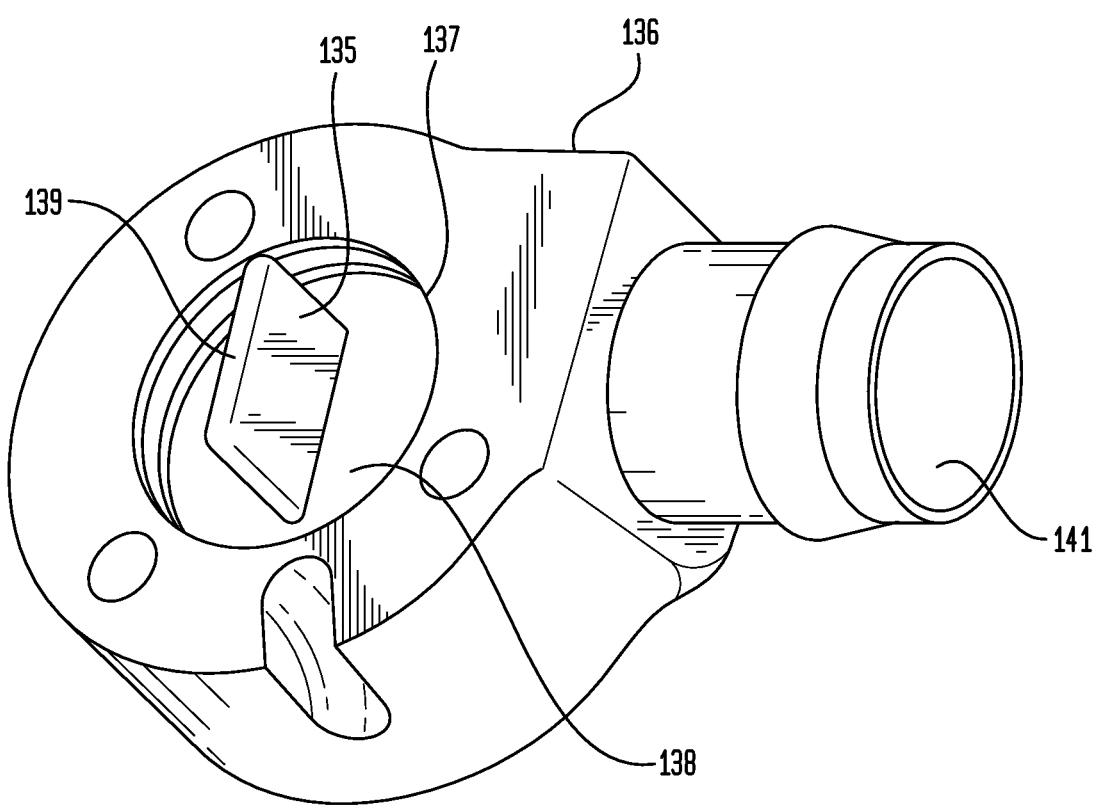
FIG. 18 is a perspective view of the interior of a volute according to a further embodiment of the present invention.

Referring to FIG. 18, there is shown still another embodiment of a volute 136 having a centrifugal flow chamber 137 of substantially circular cross section with a central axial flow straightener or stator element 135 adapted to extend generally axially into the pump chamber of an associated axial flow pump of the type described herein. The stator element 135 consists of a center post portion 138 aligned with the axis of the axial flow pump (not shown) having a tip or end portion 139 of generally rectangular shape. The short axis of the rectangular shaped stator tip is aligned and parallel with the axis of the center post portion 138 and the axis of the axial flow pump. The function of the stator element is, as described above in connection with the other volute embodiments, to alter the kinetic rotational momentum of the outflow from the pump to a pressure flow as the fluid fills the volute chamber and is pressured to discharge at the radial outlet 141.

Figure 19:
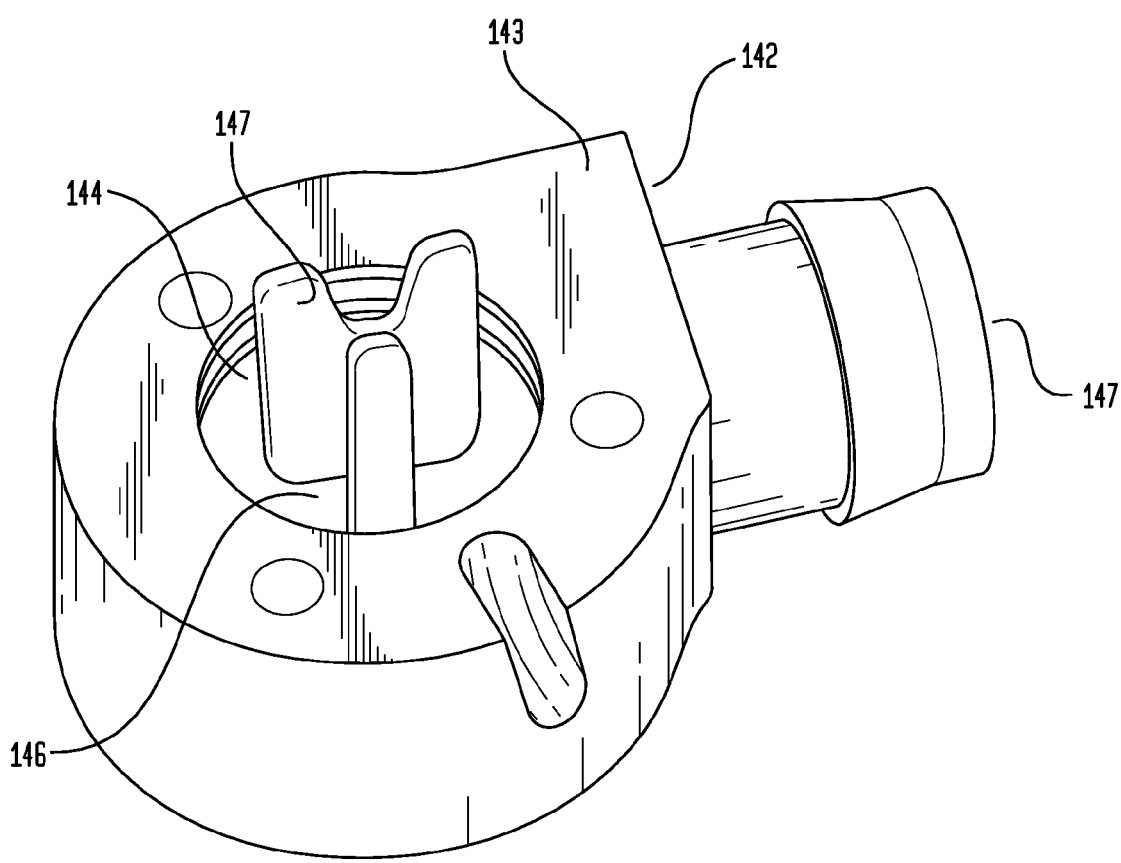
FIG. 19 is a perspective view of the interior of a volute according to yet another embodiment of the present invention.

Referring to FIG. 19, there is depicted yet another embodiment of a centrifugal volute 142 having a centrifugal flow chamber 143 of circular cross section. A flow straightener or stator element 144 extends from the base of the volute chamber axially inwardly along and substantially aligned with the axis of an associated axial flow pump (not shown). The stator element 144 consists of a central post section 146 with a wide double-tined end portion 147. Each of the tines extends generally parallel to the axis of the center post 146, one on each side thereof. Blood exiting the axial flow pump with kinetic rotational momentum is converted to a pressure flow by the stator element 144 before entering the volute chamber and being forced centrifugally to discharge from an outlet 147.

Figure 20:
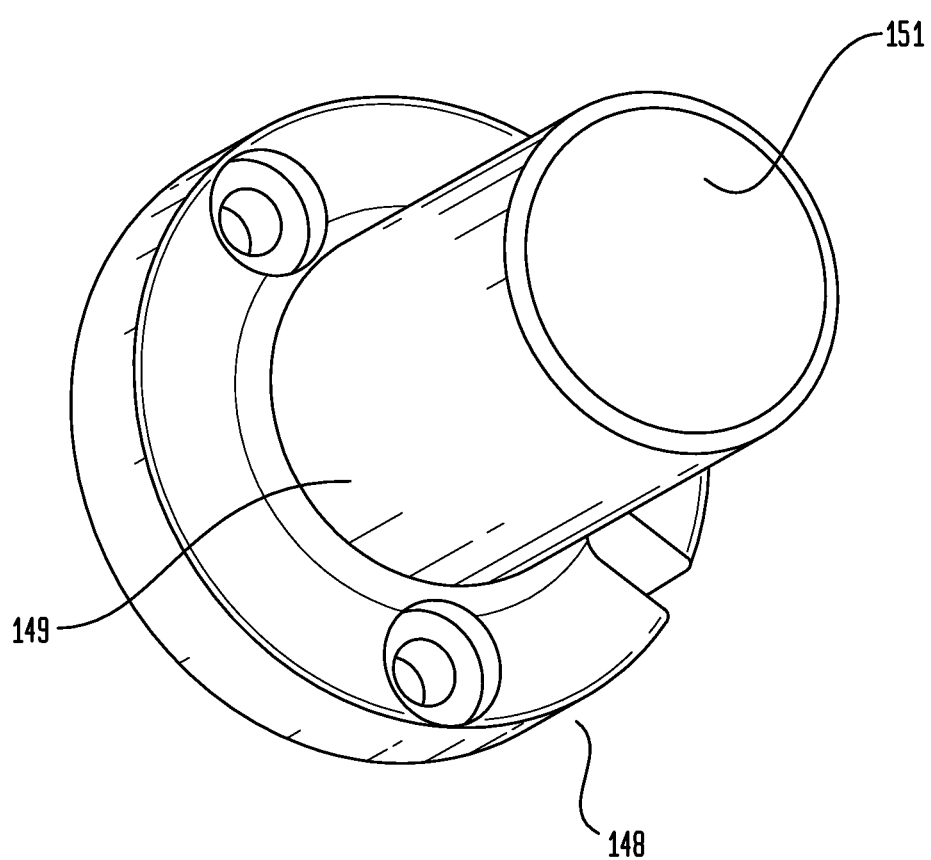
FIG. 20 is a perspective view of a downstream flow straightener according to still another embodiment of the present invention.
Figure 20A:
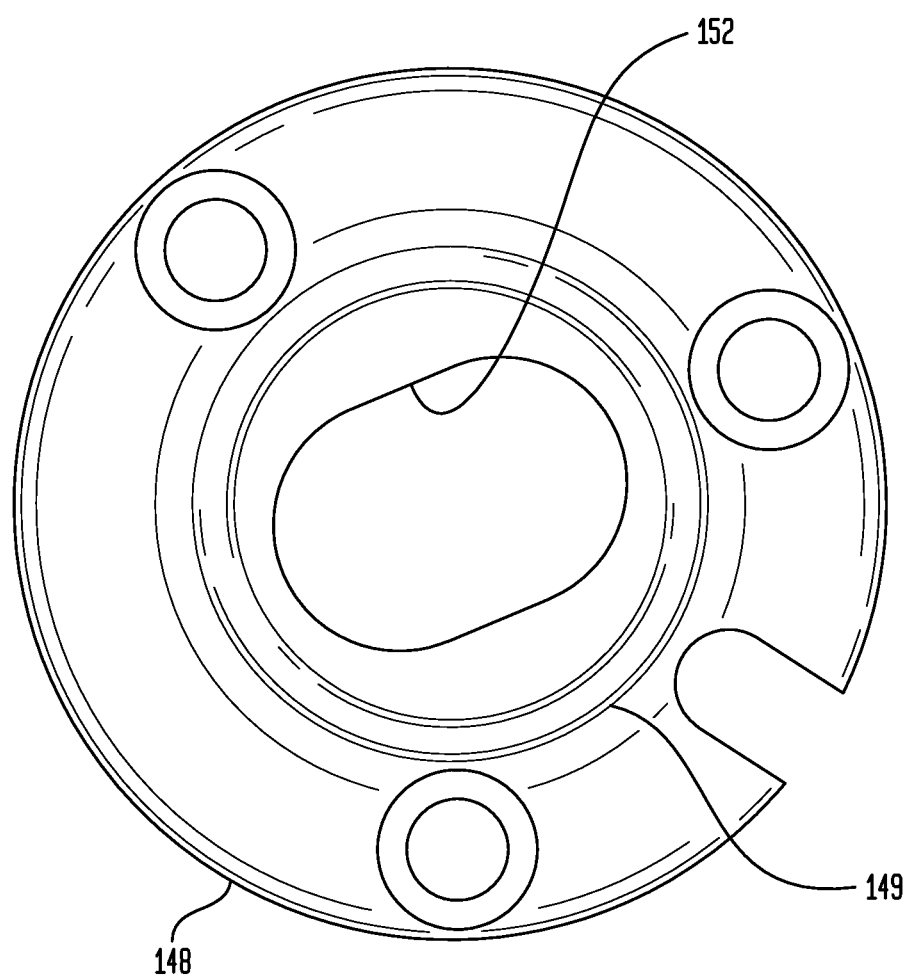
FIG. 20A is bottom elevation view of the flow straightener shown in FIG. 20.

In accordance with the present invention, blood outflow characteristics may be altered without the need for projecting blades or posts downstream of the axial flow pump. Shaped passageways designed to improve flow characteristics may be employed instead. With reference to FIGS. 20 and 20A, there is depicted a straight through flow straightener according to one embodiment of the present invention. The flow straightener has a base section 148 for securely connecting to the blood pump. A straight cylindrical tube 149 may extend from the base section 148. A passageway having a circular opening 151 may be shaped into an oval cross section with an oval outlet 152 formed within the tube 149 as shown in FIG. 20A. The opening of the shaped passageway 151 may be of any shape helping to enhance flow characteristics. The shaped passageway 161 defining the oval outlet 152 gradually ushers blood having rotational momentum through the oval-shaped constraint to convert the flow to substantially axial flow. Alternately, the shaped passageway 151 may be partially conical, having a circular, oval or other shaped outlet somewhat smaller in diameter than that of the inlet opening to accomplish the same purpose. In this embodiment, the passageway is 151 is straight and coaxial with the axis of the axial flow pump.

Figure 21:
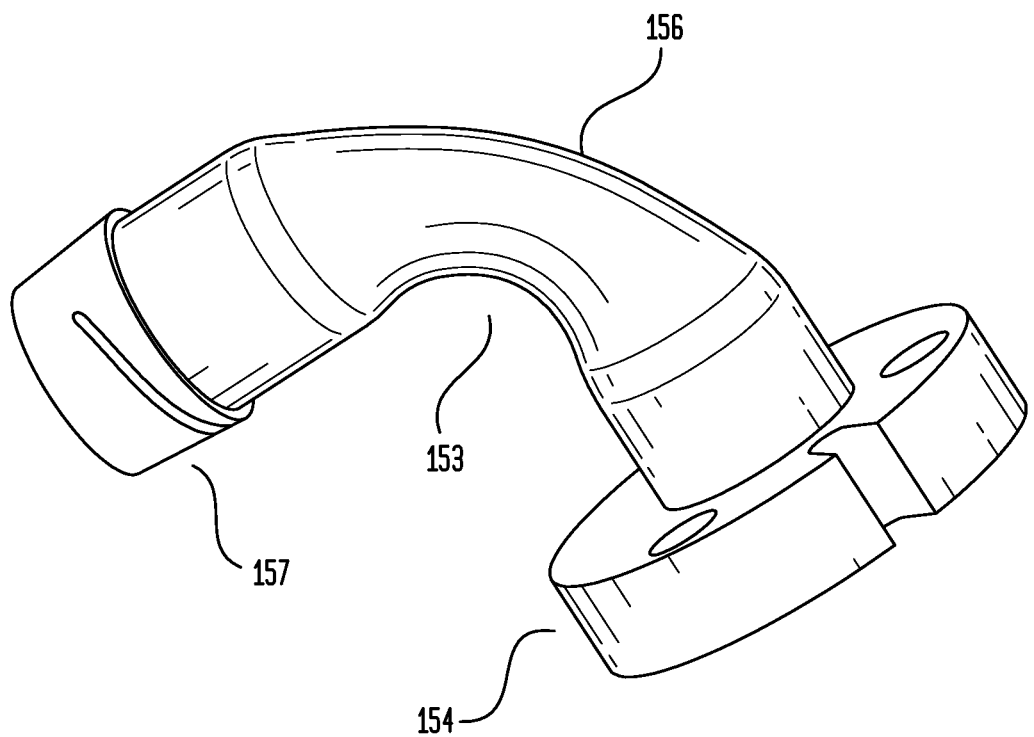
FIG. 21 is a perspective view of a downstream flow straightener according to a still further embodiment of the present invention.

With reference to FIG. 21, there is depicted a flow straightener embodiment according to a yet further embodiment of the present invention. The flow straightener of this embodiment has a base section for securely connecting to the axial flow blood pump. A bent tube 153 contains a constricted portion 156 which acts to diminish the rotational momentum of the axial blood flow output from the pump. The axial blood flow from the tube 153 is discharged through an outlet 157 from which a suitable graft will connect the blood flow to the vascular system.

Figure 22:
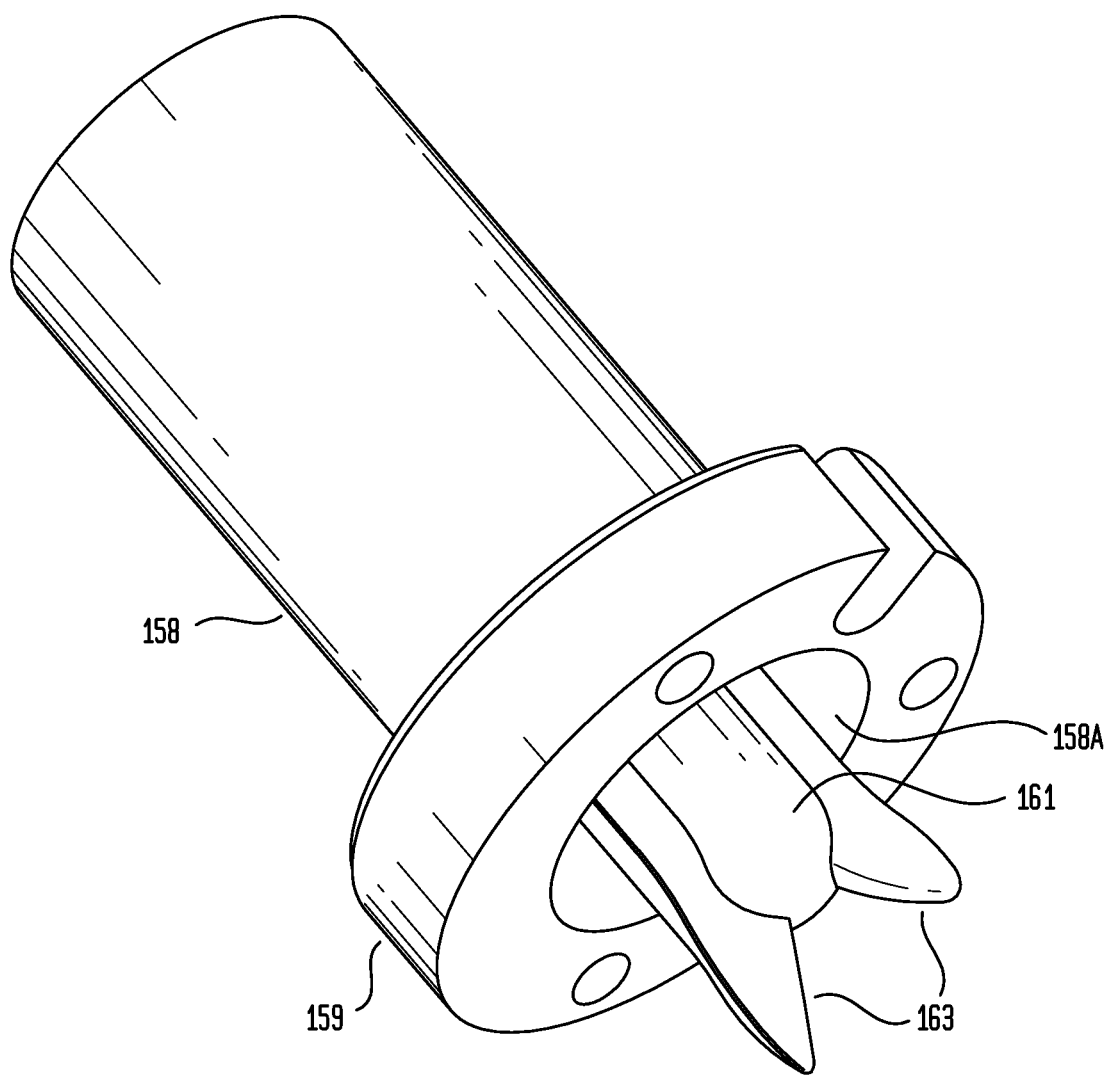
FIG. 22 is a perspective view of a downstream flow straightener according to a yet further embodiment of the present invention.
Figure 22A:
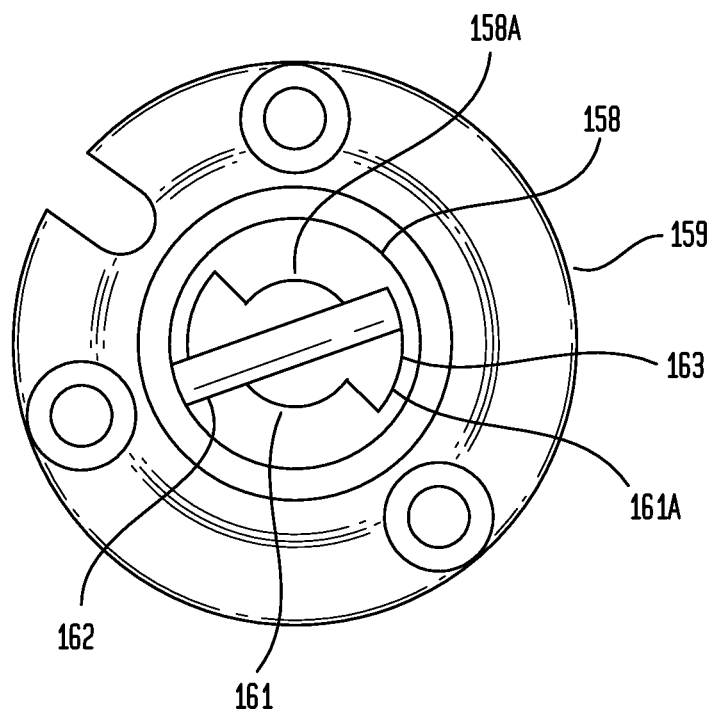
FIG. 22A is a bottom elevational view of the flow straightener shown in FIG. 22.
Figure 22B:
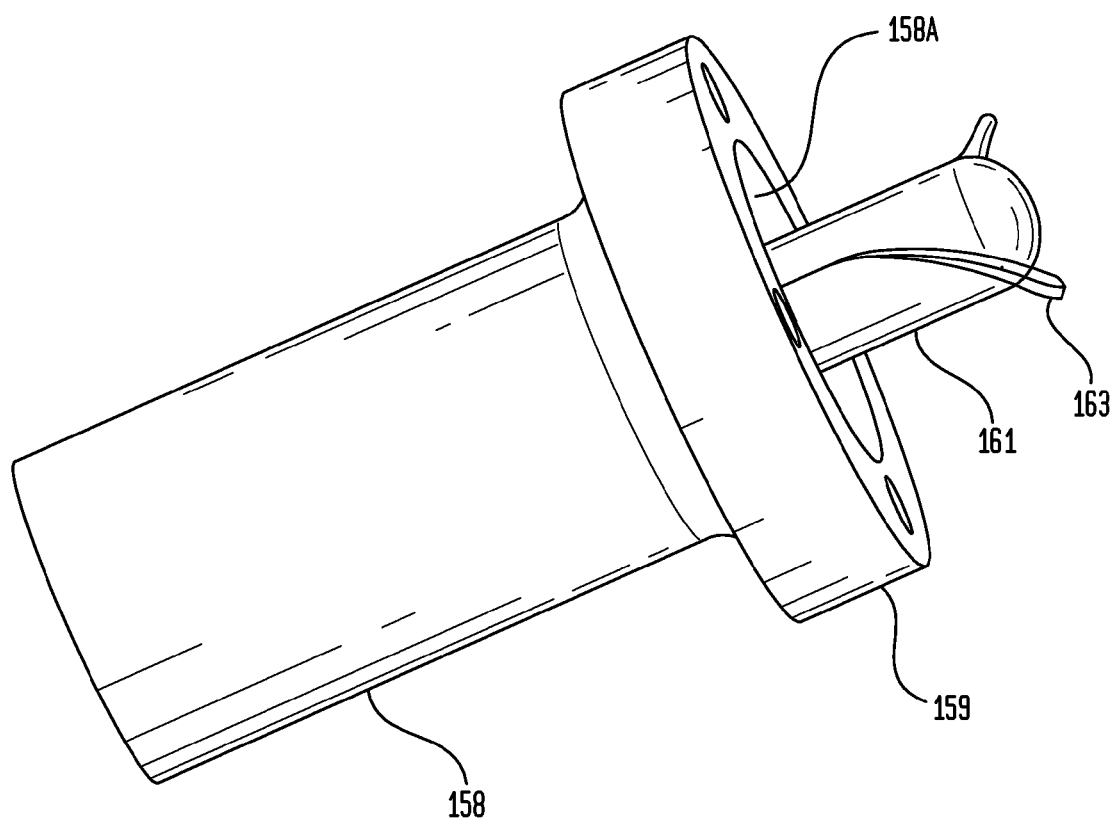
FIG. 22B is side elevation view of the flow straightener shown in FIG. 22.

Referring to FIGS. 22, 22A and 22B, there is depicted yet another embodiment of a downstream flow straightener according to the present invention. The flow straightener has a straight cylinder tube 158 having a flow chamber 158A and a base 159. A blade carrying center post 161 extends axially through at least a portion of the flow chamber 158A and extends axially into the pump chamber of an associated axial flow pump. In one embodiment, the center post 161 is affixed to the inner sidewall of the flow chamber 158A at a point of connection 162. (FIG. 22A). The support for the centerpost 162 may be a radially extending connecting arm 161A that need not traverse the entire diameter of the flow chamber. The post 161 may be of any shape, but is here depicted as a dome-topped cylinder having a pair of symmetrical diametrically opposed, contoured and pointed blade sections 163 extending longitudinally along at least part of its length and beyond by a predetermined amount. The blade sections 163 may protrude like rabbit ears beyond the top of the center post and may curve in opposite directions away from the axis of the center post 161 as depicted in FIG. 22B. The purpose of this configuration is also to diminish the rotational momentum of the axial flow output from the pump.

Figure 23:
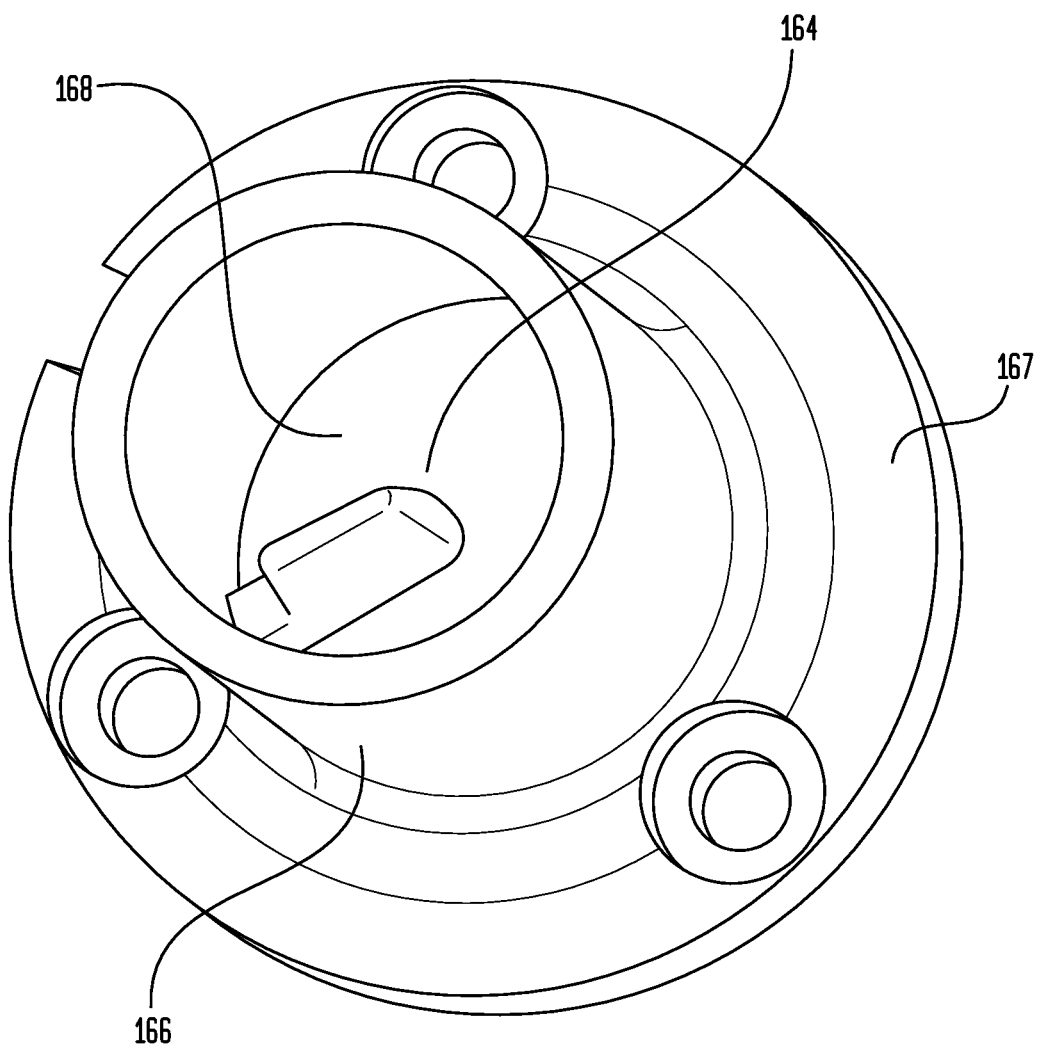
FIG. 23 is a perspective view of a downstream flow straightener according to yet another embodiment of the present invention.
Figure 23A:
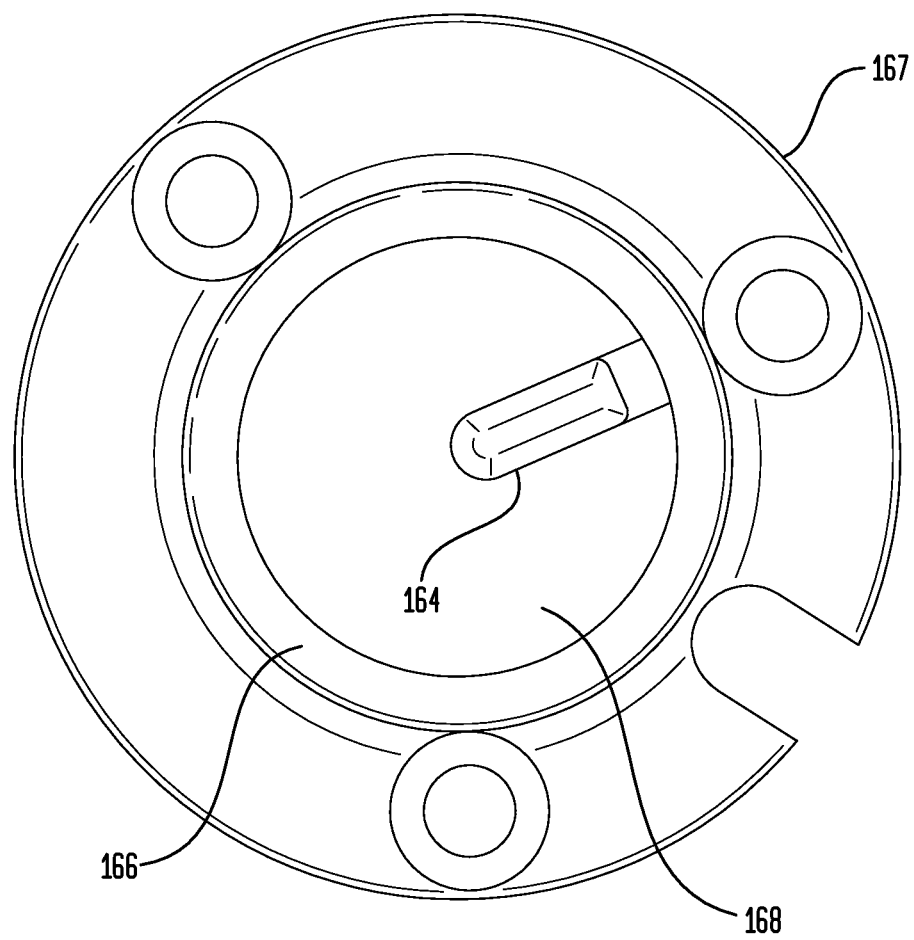
FIG. 23A is a bottom plan view of the flow straightener shown in FIG. 21A.

Referring to FIGS. 23 and 23A, there is depicted a downstream flow straightener with a simplified flow-straightening blade element 164 according to another embodiment of the present invention. In this embodiment, a straight cylindrical tube section 166 is connected to a base 167. The tube 166 is affixed at the output from an axial flow pump and defines an internal flow chamber 168. The flow-straightening blade element 164 projects radially inwardly from an inner sidewall of the flow chamber 168. The blade element 164 may be suitably welded to the sidewall of the flow chamber or be formed together with and as part of the tube section 166. The blade element 164 is configured with a transverse axis aligned parallel to or co-axial with the axis of the flow chamber 168. In one embodiment the blade element 164 terminates at about the longitudinal centerline of the flow chamber 168 (FIG. 23A). It may, however, traverse completely across the flow chamber along a diameter (not shown) without departing from the scope of the present invention. The axis of the longitudinal tube section 166 is co-axial with the axis of the axial flow pump. The blade 164 may be substantially wedge-shaped and may be short (as shown) or longer. For example, the blade 164 may extend axially through the entire length of the tube 166 and may even extend beyond the length of the tube 166, as desired. According to an embodiment of the present invention, two rotary pumps as described herein may be combined to form an artificial heart that may be used to completely replace the natural heart in a patient suffering from heart failure.

Figure 24:
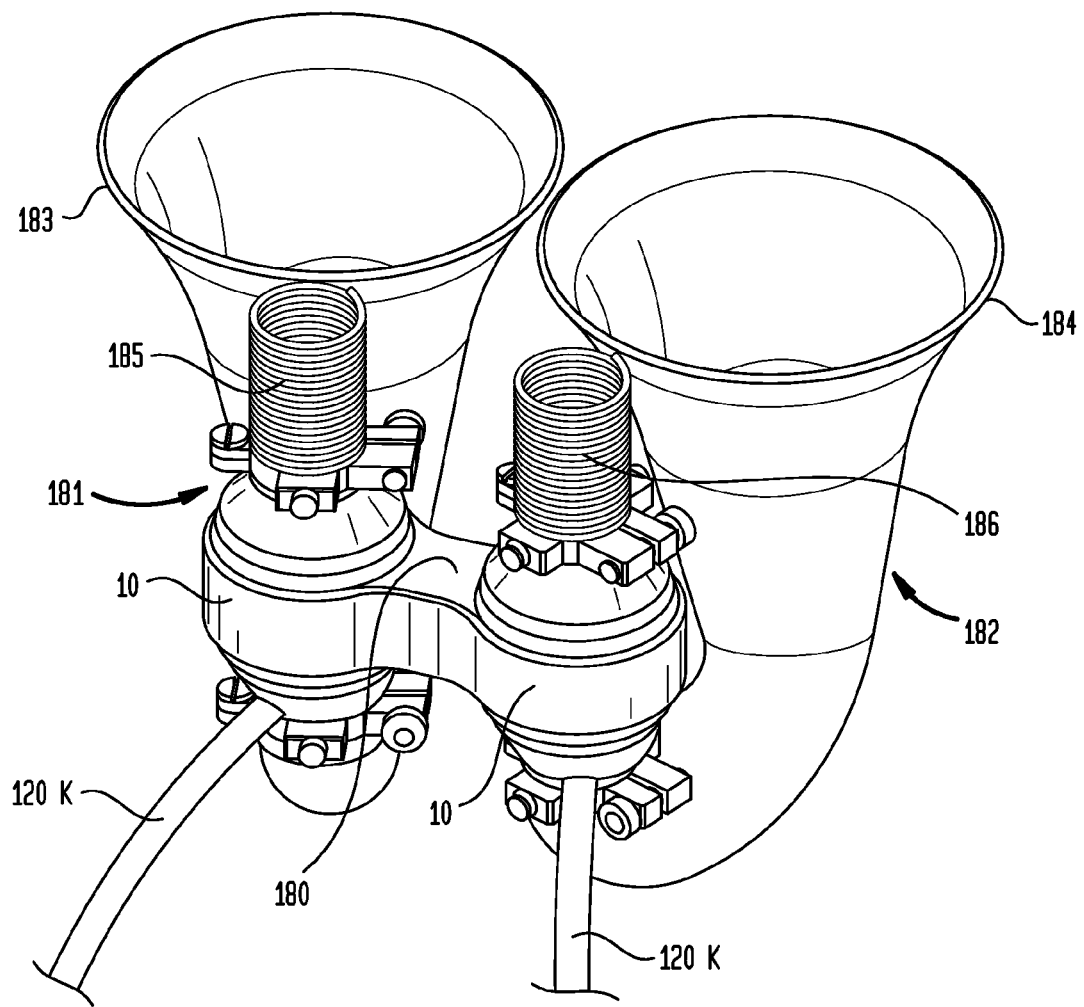
FIG. 24 is a perspective view of an artificial heart utilizing axial flow rotary pumps of the type shown and described herein.

Referring to FIG. 24, an artificial heart is shown using rotary axial flow blood pumps of the type described herein. In one embodiment, the artificial heart may comprise a first section 181 for pumping blood to the patient's aorta and a second section 182 for pumping blood to the patient's pulmonary artery. Each section 181 and 182 may contain a pump 10 as described in detail above. The first section 181 may include a first inflow 183 and a first outflow 185. The second section 182 may include a second inflow 184 and a second outflow 186.

The inflows 183 and 184 may be made of a penetrable material such as a soft Dacron texture material so that it may be easily sutured to the patient's circulatory system. The inflows 183 and 184 may have a shape that is wider at the end that is connected to the patient's circulatory system than at the end that is connected to the pump 10. The inflows 183 and 184 may be elbowed so that the inflows 183 and 184 may be proximal to the outflows 185 and 186.

The first pump section 181 and the second pump section 182 may be attached together by a connecting member 180 such as a bracket or the like.

In this embodiment, the artificial heart does not require artificial vales thereby improving device reliability.

A balance member or atrial shunt or shunt may optionally be connected between the first and second inflows 183 and 184 to substantially equalize or balance the flow of blood through the first and second inflows 183 and 184. Thus, when the pressure in the first and second inflow members is unbalanced, blood may be shunted between the inflow members. The shunt may include two ends where one of the ends is connected to the first inflow 183 and the opposing end of the shunt is connected to the second inflow 184. The shunt 124 may be integrally formed with each of the inflows 183 and 184. The shunt may automatically equalize or balance the hydraulic blood flow through each of the first and second sections 181 and 182. The shunt may therefore prevent one side of the artificial heart from over pumping the other side of the heart The first section 181 may be designed to pump more blood than the section 184. According to one embodiment, the first section 183 is designed to pump 15% more blood than the second section 182.

Power and control cables 120K may be used to power and control each pump 10.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. An axial flow blood pump, comprising:
   a pump housing;
   a rotor for pumping blood positioned in said housing, said rotor having an axis of rotation, a leading edge proximate an upstream end of said rotor, and a trailing edge proximate a downstream end of said rotor, and comprising peripheral land surfaces defined by one or more flow channels between the respective land surfaces, said one or more flow channels extending from said leading edge to said trailing edge, each said one or more flow channels being curved and having a substantially axially extending outlet channel proximate said trailing edge to drive blood in an axial direction as the rotor is rotated, wherein a collective width of said channels in a circumferential direction of said rotor at each of some axial positions on the radial periphery of the rotor being substantially equal to or less than the collective total width of said peripheral land surfaces in the circumferential direction at said axial positions; and
   a motor including a plurality of magnetic poles carried by the rotor, and a stator including an electrically activated coil to magnetically interact with said magnetic poles to cause said rotor to rotate.

2. The axial flow blood pump of claim 1, wherein the coil of the stator is positioned radially outward from the radial periphery of the rotor and the housing, wherein the coil is configured to create magnetic flux under application of electric power thereto, the magnetic flux coupled to said peripheral land surfaces of said rotor.

3. The axial flow blood pump of claim 2 in which the motor comprises a stator enclosure that slides over said pump housing and is hermetically sealed thereto, the coil positioned within the stator enclosure.

4. The for axial flow blood pump of claim 1 in which the rotor is provided with a plurality of bores therein to provide dynamic balance during rotation thereof.

5. The axial flow blood pump of claim 1 in which said one or more flow channels are of non-uniform depth along a length from said upstream end of said rotor to said downstream end thereof.

6. The axial flow blood pump of claim 5 in which the average depth of each of said one or more flow channels from the peripheral land surfaces is within a range of from about 1 mm to about 5 mm.

7. The axial flow blood pump of claim 5 in which each of said one or more flow channels includes a fluid entry opening proximate said leading edge, wherein a depth of one or more flow channels is greater at said fluid entry openings than at said outlet channels.

8. The axial flow blood pump of claim 1 in which said rotor comprises a heat treated biomedical magnetic alloy.

9. The axial flow blood pump of claim 8 in which said rotor is made from ferromagnetic material comprising an alloy of platinum and cobalt of about 70-80% platinum by weight and about 20-30% cobalt by weight, said pump housing being made from biocompatible titanium or ceramic.

10. The axial flow blood pump of claim 8 wherein at least portions of each of said peripheral land surfaces are magnetized to provide electromagnetic coupling with said motor stator.

11. The axial flow blood pump of claim 2 in which peripheral land areas of said rotor corresponding to said land surfaces contain drive magnets and said motor stator comprises a plurality of the electrically activated coils surrounding said drive magnets to rotate said rotor by application of electric power to said coils to create magnetic flux with respect to said drive magnets.

12. The axial flow blood pump of claim 1 comprising orientation magnetic poles on peripheral land areas of the rotor corresponding to said land surfaces at locations proximate at least one of the leading or trailing edges of the rotor, and corresponding stator magnetic poles adjacent said orientation magnetic poles such that a pair of a stator magnetic pole and a corresponding orientation magnetic pole adjacent thereto repel one another to provide orienting axial support for said rotor within said pump housing.

13. The axial flow blood pump of claim 1 in which said one or more outlet channels are wider than curved portions of said one or more curved fluid flow channels.

14. The axial flow blood pump of claim 1 in which an interior wall surface of said pump housing adjacent said leading edge defines an inwardly constricting annular inlet ring, said leading edge of said rotor being contoured to follow a downstream shape of said annular inlet ring to assist in positioning the rotor within said pump housing.

15. The axial flow blood pump of claim 14 in which said contoured leading edge of said rotor is provided with a hydrodynamic thrust bearing surface to cooperate with said downstream shape of said annular inlet ring to assist in positioning the rotor within the pump housing.

16. The axial flow blood pump of claim 1 in which one or more hydrodynamic thrust bearing surfaces are disposed substantially circumferentially at each of said peripheral land surfaces, each of said thrust bearing surfaces having a leading front end recessed relative to said radial periphery of said rotor from which said thrust bearing surface tapers in a gradual curved manner to a trailing rear end thereof to transition into said radial periphery, wherein a gap between said peripheral land surface and an interior wall surface of said pump housing is larger at said leading front end than at said trailing rear end for hydrodynamic thrust control of the position of said rotor within said pump housing.

17. The axial flow blood pump of claim 16 in which each of said thrust bearing surfaces tapers along an arc not coaxial with the rotational axis of the rotor and comprises a shroud along each lateral side thereof to reduce fluid leakage therefrom, each of said shrouds decreasing in height relative to said thrust bearing surface from said leading front end to said trailing rear end thereof.

18. The axial flow blood pump of claim 17 in which each of said shroud sidewalls extends substantially transverse to the rotational axis of the rotor.

19. The axial flow blood pump of claim 16 in which a relief portion of each peripheral land surface contiguous with said trailing rear end of a thrust bearing surface diverges to enlarge said gap to reduce pressure on blood therein.

20. The axial flow blood pump of claim 1 in which an interior wall surface of said pump housing is constricted adjacent said trailing edge to define an annular outlet ring, said trailing edge of said rotor being contoured to follow an upstream shape of said annular outlet ring.

* * * * *